United States Patent
Rapoport

(10) Patent No.: US 10,383,762 B2
(45) Date of Patent: Aug. 20, 2019

(54) PASSIVE THERMO-REGULATED NEONATAL TRANSPORT INCUBATOR

(71) Applicant: Aspect Imaging Ltd., Shoham (IL)

(72) Inventor: Uri Rapoport, Moshav Ben Shemen (IL)

(73) Assignee: ASPECT IMAGING LTD., Shoham (IL)

( * ) Notice: Subject to any disclaimer, the term of this patent is extended or adjusted under 35 U.S.C. 154(b) by 215 days.

(21) Appl. No.: 14/915,906

(22) PCT Filed: Sep. 2, 2014

(86) PCT No.: PCT/IL2014/050786
§ 371 (c)(1),
(2) Date: Mar. 2, 2016

(87) PCT Pub. No.: WO2015/029045
PCT Pub. Date: Mar. 5, 2015

(65) Prior Publication Data
US 2016/0206493 A1    Jul. 21, 2016

Related U.S. Application Data

(60) Provisional application No. 61/872,793, filed on Sep. 2, 2013, provisional application No. 61/879,154, filed (Continued)

(51) Int. Cl.
*A61G 11/00* (2006.01)
*A61F 7/00* (2006.01)
(Continued)

(52) U.S. Cl.
CPC .......... *A61F 7/0053* (2013.01); *A61B 5/0555* (2013.01); *A61G 11/00* (2013.01);
(Continued)

(58) Field of Classification Search
CPC ............................................... A61G 11/00–009
(Continued)

(56) References Cited

U.S. PATENT DOCUMENTS

| 1,900,342 | A | * | 3/1933 | Hess | ............... | A61G 11/00 600/22 |
| 2,401,605 | A | | 6/1946 | Boren | | |

(Continued)

FOREIGN PATENT DOCUMENTS

| CA | 2815746 | 5/2012 |
| CN | 2448344 | 9/2001 |

(Continued)

OTHER PUBLICATIONS

Antonucci, et al., The infant incubator in the neonatal intensive care unit: unresolved issues and future developments, J. Perinat. Med. 37(2009), 587-598.

(Continued)

*Primary Examiner* — Catherine B Kuhlman
(74) *Attorney, Agent, or Firm* — Pearl Cohen Zedek Latzer Baratz LLP

(57) ABSTRACT

A passive neonatal transport incubator (PNTI), useful for thermo-regulating a neonate, comprising an inner volume configured by means of size and shape to accommodate the neonate, the inner volume is defined by an envelope having a main longitudinal axis with a proximal end and an opposite distal end, the envelope is at least partially perforated. Further, the PNTI is configured to be ventilated by an independently ventilated medical device, and is configured by means of size, shape and material to allow the neonate to be examined by the medical device.

17 Claims, 12 Drawing Sheets

Related U.S. Application Data on Sep. 18, 2013, provisional application No. 61/893,959, filed on Oct. 22, 2013, provisional application No. 61/902,236, filed on Nov. 10, 2013, provisional application No. 61/902,314, filed on Nov. 11, 2013.

(51) Int. Cl.

| | | |
|---|---|---|
| *G10K 11/162* | (2006.01) | |
| *G10K 11/175* | (2006.01) | |
| *A61M 16/16* | (2006.01) | |
| *A61B 5/055* | (2006.01) | |
| *A61M 16/10* | (2006.01) | |
| *A61M 16/00* | (2006.01) | |
| *G10K 11/168* | (2006.01) | |
| *G10K 11/172* | (2006.01) | |
| *G10K 11/20* | (2006.01) | |
| *G01H 3/14* | (2006.01) | |

(52) U.S. Cl.
CPC ...... *A61M 16/0003* (2014.02); *A61M 16/105* (2013.01); *A61M 16/161* (2014.02); *G10K 11/162* (2013.01); *G10K 11/175* (2013.01); *A61B 2503/045* (2013.01); *A61F 2007/006* (2013.01); *A61F 2007/0054* (2013.01); *A61F 2007/0055* (2013.01); *A61F 2007/0057* (2013.01); *A61F 2007/0093* (2013.01); *A61F 2007/0095* (2013.01); *A61G 11/009* (2013.01); *A61G 2200/14* (2013.01); *A61G 2203/30* (2013.01); *A61G 2203/36* (2013.01); *A61G 2203/44* (2013.01); *A61G 2203/46* (2013.01); *A61G 2203/70* (2013.01); *A61G 2210/50* (2013.01); *A61M 2016/0027* (2013.01); *A61M 2205/0233* (2013.01); *A61M 2205/3633* (2013.01); *A61M 2205/42* (2013.01); *G01H 3/14* (2013.01); *G10K 11/168* (2013.01); *G10K 11/172* (2013.01); *G10K 11/20* (2013.01); *G10K 2210/116* (2013.01); *G10K 2210/118* (2013.01); *G10K 2210/129* (2013.01); *G10K 2210/301* (2013.01); *G10K 2210/3223* (2013.01); *G10K 2210/3224* (2013.01); *G10K 2210/509* (2013.01)

(58) Field of Classification Search
USPC .......................................................... 600/22
See application file for complete search history.

(56) References Cited

U.S. PATENT DOCUMENTS

| | | |
|---|---|---|
| 2,633,842 A | 4/1953 | Higgs |
| 2,638,087 A | 5/1953 | Livsey et al. |
| 2,708,927 A | 5/1955 | Dixon et al. |
| 3,012,836 A | 12/1961 | Smith et al. |
| 3,315,671 A | 4/1967 | Creelman |
| 3,470,866 A | 10/1969 | Gittelson |
| 3,655,178 A | 4/1972 | Vezina |
| 3,710,791 A | 1/1973 | Deaton |
| 3,920,000 A | 11/1975 | Atherton et al. |
| 4,161,172 A | 7/1979 | Pickering |
| 4,509,505 A | 4/1985 | Mercey et al. |
| 4,567,894 A | 2/1986 | Bergman |
| 4,712,263 A | 12/1987 | Pronzinski |
| 4,750,474 A | 6/1988 | Dukhan et al. |
| 4,936,824 A * | 6/1990 | Koch .................. A61G 11/00 128/205.26 |
| 5,028,872 A | 7/1991 | Nakabayashi |
| 5,059,906 A | 10/1991 | Yamanaka |
| 5,100,375 A | 3/1992 | Koch |
| 5,446,934 A | 9/1995 | Frazier |
| 5,534,669 A | 7/1996 | Schroeder et al. |
| 5,759,149 A | 6/1998 | Goldberg et al. |
| 5,797,833 A | 8/1998 | Kobayashi et al. |
| 5,800,335 A | 9/1998 | Koch et al. |
| 5,817,003 A | 10/1998 | Moll et al. |
| 5,917,324 A | 6/1999 | Leussler |
| 5,943,716 A | 8/1999 | Chu |
| 5,971,913 A | 10/1999 | Newkirk et al. |
| 6,036,634 A | 3/2000 | Goldberg et al. |
| 6,155,970 A | 12/2000 | Dykes et al. |
| 6,231,499 B1 | 5/2001 | Jones |
| D446,675 S | 8/2001 | Straub |
| 6,317,618 B1 | 11/2001 | Livni et al. |
| 6,409,654 B1 | 6/2002 | McClain et al. |
| 6,433,548 B1 | 8/2002 | Furuta et al. |
| 6,471,634 B1 | 10/2002 | Dykes et al. |
| 6,511,414 B1 | 1/2003 | Hamsund |
| 6,611,702 B2 | 8/2003 | Rohling et al. |
| 6,641,521 B2 | 11/2003 | Kolarovic |
| 6,666,816 B2 | 12/2003 | Mountain |
| RE38,453 E | 3/2004 | Lessard et al. |
| 6,776,527 B1 | 8/2004 | Tybinkowski |
| 6,860,272 B2 | 3/2005 | Carter et al. |
| 6,992,486 B2 | 1/2006 | Srinivasan |
| 7,255,671 B2 | 8/2007 | Boone et al. |
| 7,278,962 B2 | 10/2007 | Lonneker-Lammers |
| D567,948 S | 4/2008 | Tierney et al. |
| 7,482,558 B2 | 1/2009 | Koch |
| 7,599,728 B2 | 10/2009 | Feenan |
| 7,719,279 B2 | 5/2010 | Rapoport |
| 7,784,121 B2 | 8/2010 | Ahlman |
| 8,147,396 B2 | 4/2012 | Srinivasan |
| 8,461,841 B2 | 6/2013 | Rapoport et al. |
| 9,974,705 B2 | 3/2018 | Rapoport |
| 2001/0049465 A1 | 12/2001 | Goldberg et al. |
| 2002/0072648 A1 | 6/2002 | Dykes et al. |
| 2002/0123681 A1 | 9/2002 | Zuk et al. |
| 2002/0143233 A1 | 10/2002 | Donnelly et al. |
| 2002/0173696 A1 | 11/2002 | Kolarovic et al. |
| 2002/0173717 A1 | 11/2002 | Rohling et al. |
| 2003/0088175 A1 | 5/2003 | Branch et al. |
| 2004/0030241 A1 | 2/2004 | Green et al. |
| 2004/0034273 A1 | 2/2004 | Boris |
| 2004/0133064 A1 | 7/2004 | Castillon Levano et al. |
| 2004/0186341 A1 | 9/2004 | McDermott |
| 2004/0236174 A1 | 11/2004 | Boone et al. |
| 2004/0236175 A1 | 11/2004 | Boone et al. |
| 2005/0004422 A1* | 1/2005 | Caspary ................ A61G 11/00 600/21 |
| 2005/0020906 A1 | 1/2005 | Seijger et al. |
| 2005/0038314 A1 | 2/2005 | Falk |
| 2005/0113668 A1* | 5/2005 | Srinivasan ............ A61B 5/055 600/411 |
| 2006/0079730 A1 | 4/2006 | Getsla |
| 2007/0232894 A1 | 10/2007 | Feenan |
| 2008/0163425 A1 | 7/2008 | White |
| 2009/0044335 A1 | 2/2009 | Brewin et al. |
| 2009/0209846 A1 | 8/2009 | Bammer |
| 2010/0004502 A1 | 1/2010 | Honma et al. |
| 2010/0168502 A1 | 7/2010 | Delaporte et al. |
| 2011/0048424 A1 | 3/2011 | Radko |
| 2011/0113555 A1 | 5/2011 | Smith |
| 2011/0125010 A1 | 5/2011 | Vaquero Lopez et al. |
| 2011/0160521 A1 | 6/2011 | Khodak et al. |
| 2012/0078034 A1* | 3/2012 | Falk .................... A61G 11/00 600/22 |
| 2012/0126814 A1 | 5/2012 | Fischer et al. |
| 2013/0025062 A1 | 1/2013 | Esch |
| 2013/0109956 A1 | 5/2013 | Rapoport |
| 2013/0150656 A1 | 6/2013 | Falk et al. |
| 2013/0204074 A1 | 8/2013 | Belvar et al. |
| 2013/0204617 A1 | 8/2013 | Kuo et al. |
| 2013/0267765 A1 | 10/2013 | Rapoport |
| 2013/0334439 A1 | 12/2013 | Etters |
| 2014/0003614 A1 | 1/2014 | Levitov et al. |
| 2014/0051976 A1 | 2/2014 | Rapoport et al. |
| 2014/0078301 A1 | 3/2014 | Fazzi et al. |
| 2014/0098934 A1 | 4/2014 | Kondo |
| 2014/0099010 A1 | 4/2014 | Rapoport |
| 2014/0117989 A1 | 5/2014 | Rapoport |

(56) References Cited

U.S. PATENT DOCUMENTS

| | | | |
|---|---|---|---|
| 2014/0354279 | A1 | 12/2014 | Dumoulin et al. |
| 2014/0357981 | A1 | 12/2014 | Dumoulin |
| 2014/0364722 | A1 | 12/2014 | Dumoulin |
| 2015/0137812 | A1 | 5/2015 | Rapoport |
| 2015/0141799 | A1 | 5/2015 | Rapoport et al. |
| 2016/0030264 | A1 | 2/2016 | Lehmann et al. |
| 2016/0081582 | A1 | 3/2016 | Rapoport |

FOREIGN PATENT DOCUMENTS

| | | |
|---|---|---|
| CN | 102551719 | 7/2012 |
| DE | 19617739 | 6/1997 |
| EP | 1132072 | 9/2001 |
| EP | 2581071 | 4/2013 |
| IL | 226488 | 11/2016 |
| JP | 2004531313 | 10/2004 |
| JP | 2005514078 | 5/2005 |
| JP | 2007252741 | 10/2007 |
| JP | 2010178857 | 8/2010 |
| JP | 2016539683 | 12/2016 |
| WO | WO 98/48756 A1 | 11/1998 |
| WO | WO9921526 | 5/1999 |
| WO | WO2008137003 | 11/2008 |
| WO | WO2010054457 | 5/2010 |
| WO | WO2011109761 | 9/2011 |
| WO | WO2012143825 | 10/2012 |
| WO | WO2013115847 | 8/2013 |

OTHER PUBLICATIONS

Baby Pod II Infant Transport Device, Advance Healthcare Technology, brochure, pp. 1-6.
Baby Pod II Operation and Maintenance Manual, revision 5, Jan. 2011, pp. 1-11.
Ferris et al., The design of neonatal incubators: a systems-oriented, human centered approach, J. Perinatology, 2013, 33, S24-S31.
Kitterman et al., Catheterization of umbilical vessels in newborn infants, Pediatric Clinics of North America, vol. 17, No. 4, Nov. 1970, 895-912.
Paley et al., An MR-compatible neonatal incubator, The British Journal of Radiology, 85, 2012, 952-958.
American National Standard, Medical Electrical Equipment—Parts 2-19: Particular requirements for the basic safety and essential performance of infant incubators, Association for the advancement of medical instrumentation, ANSI/AAI/IEC 60601-2-19:2009, pp. 1-19.
Jenkins, S., ScanPod, BabyPod-Products-ScanPod, 2002-2011 Advance Healthcare Technology, ltd., internet website http://babypod.com:80/products/scanpod.php.
Science Daily, Inside the preemie brain, Incubator enables MRI scans on premeeies for preventing birth asphyxia, Dec. 1, 2005, pp. 1-2, Web address: http://web.archive.org/web/20130303154220/http://www.sciencedaily.com/videos/2005/1211-inside_the_preemie_brain.htm.
Thermaxx Jackets, 5 most common thermal insulation materials, pp. 1-4, internet: https://wvvw.thermaxxjackets.com/5-most-common-thermal-insulation-materials/.
U.S. Appl. No. 61/994,901 filed May 18, 2014, Rapoport.
Marik et al. "Neonatal incubators: a toxic sound environment for the preterm infant?", Pediatr Crit Care Med, Nov. 2012; Vo. 13(6): pp. 685-689.
International Search Report for PCT application No. PCT/IL2014/050787, dated Dec. 30, 2014.
Ranganna et al. "Reducing noise on the neonatal unit", Infant, vol. 7, Issue 1, pp. 25-28, 2011.
Mahil et al. "Hybrid Swarm Algorithm for the Suppression of Incubator Interference in Premature Infants ECG", Research Journal of Applied Sciences, Engineering and Technology 6(16): 2931-2935, Sep. 10, 2013.
Brown G. "NICU noise and the preterm infant", Neonatal Network, 2009, vol. 28(3): pp. 165-173.
Sang-Hoon Kim. "Air transparent soundproof window", Air Advances, vol. 4, 1171232014.
International Search Report for PCT application No. PCT/IL2014/050786, dated Dec. 30, 2014.
Lichuan Liu et al."Development and applications of active noise control system for infant incubators" Proceedings of the 2009 IEEE International Conference on Systems, Man and Cybernetics, TX, USA, Oct. 2009 pp. 2659-2664.
International Search Report for PCT application No. PCT/IL2014/050785, dated Jun. 8, 2015.
Knutson, A. J. et al "Acceptable noise levels for neonates in the neonatal intensive care unit"., Washington University School of Medicine, 2013.

* cited by examiner

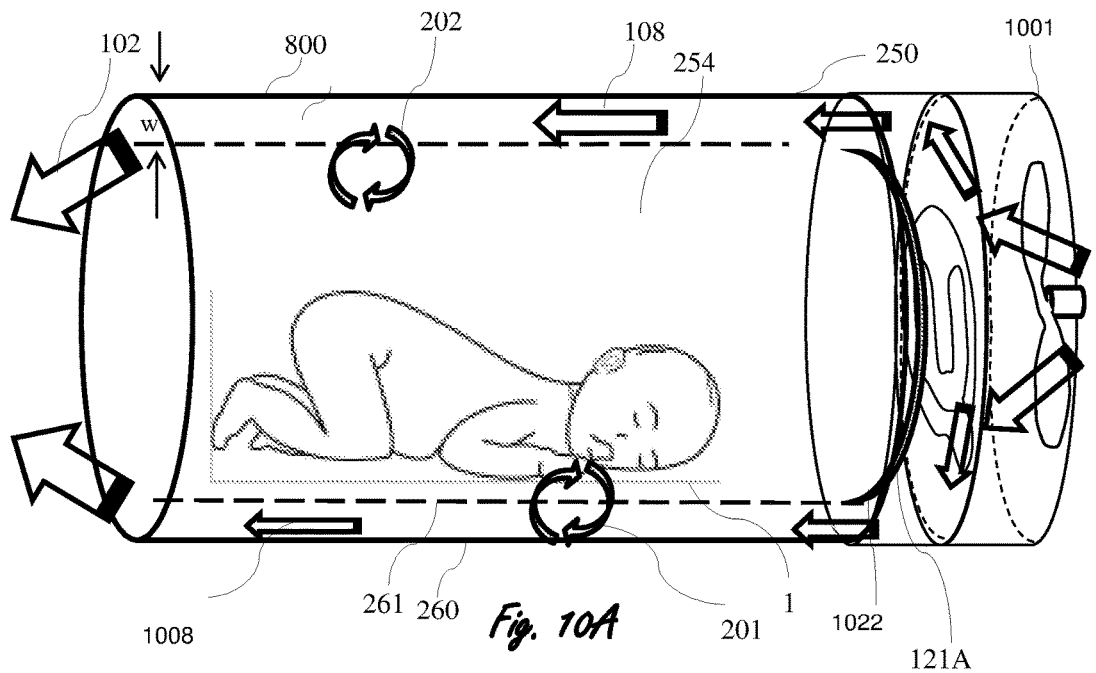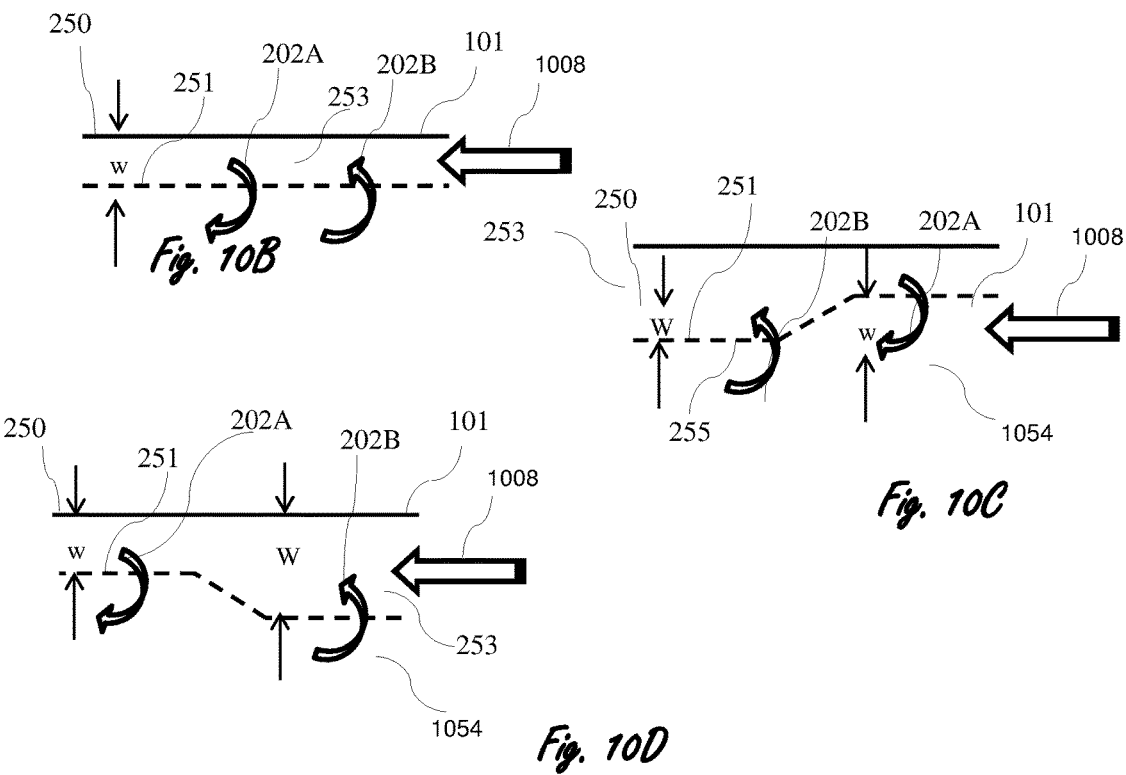
Fig. 10A
Fig. 10B
Fig. 10C
Fig. 10D

PASSIVE THERMO-REGULATED NEONATAL TRANSPORT INCUBATOR

CROSS-REFERENCE TO RELATED APPLICATIONS

This application is a National Phase Application of PCT International Application No. PCT/IL2014/050786, International Filing Date Sep. 2, 2014, claiming the benefit of U.S. Provisional Patent Application No. 61/902,314 filed Nov. 11, 2013, of U.S. Provisional Patent Application No. 61/902,236 Nov. 10, 2013, of U.S. Provisional Patent Application No. 61/893,959 filed Oct. 22, 2013, of U.S. Provisional Patent Application No. 61/879,154 filed Sep. 18, 2013 and of U.S. Provisional Patent Application No. 61/872,793 filed Sep. 2, 2013, all of which are hereby incorporated by reference.

FIELD OF THE INVENTION

The present invention generally pertains to a vented and thermo-regulated environment of a neonate, especially incubators and system in connection with the same. More specifically, the invention relates to a passive neonatal transport incubator (PNTI) which is MRI-safe.

BACKGROUND OF THE INVENTION

When treating and handling newborn babies and especially neonates, it is imperative that they are kept in life supporting conditions. These include maintaining the neonate in a steady appropriate temperature and providing a constant supply of fresh air, with an adequate percentage of the comprising gases.

In order to control the environment of neonates when in a care taking facility, they are usually kept in incubators where the physical conditions of the neonate and surroundings are controlled and monitored. Oxygenation, can be supplied through oxygen supplementation by head hood or nasal cannula, or even continuous positive airway pressure (CPAP) or mechanical ventilation. In addition, it is important to recycle and circle air through the incubator to insure the appropriate concentration of the various comprising gases. In many times the circling air is humidified and/or used to heat the incubator.

In closed incubators, providing an optimal thermal environment is a priority not only for survival and growth but also for the stability of various physiological functions.

It was stated in the art that the most common way for regulating the heating of air circulating through an incubator is to control the power delivered to the heater. U.S. Pat. No. RE38,453 which is incorporated herein as a reference, discloses an infant incubator, constructed in accordance with the present invention, includes a hood having an access door in a wall thereof and a base upon which the hood is mounted and having a deck which with the hood defines an enclosure. The deck has openings through which air enters and leaves the enclosure. Also included in this incubator is a heater within the base for heating the air and a fan for supplying air to the heater and forwarding the heated air from the heater into the enclosure through at least one of the openings and for returning air from the enclosure to the heater through at least one of the openings. An infant incubator, constructed in accordance with the present invention, further includes sensing means responsive to movement of the access door for sensing when the access door is opened and control means responsive to the sensing means for increasing the heat generated by the heater and increasing the speed of the fan when the access door is opened. Similar technology is disclosed in U.S. Pat. Nos. 6,036,634 and 6,641,521 which are also incorporated herein as references. U.S. Pat. No. 6,511,414 which is also incorporated herein as a reference discloses a neonate's incubator in which thermo-regulated air flows upwardly from air inlet ducts in the base of the incubator, this flow is relatively noisy and can disturb the wellbeing of the neonate.

Noise is well-documented in the art to be a stress inducing factor for neonates that can hinder development. As published in Neonatal Network, 2009 28(3):165-173, by Brown G., titled: "NICU noise and the preterm infant", preterm infants exposed to prolonged excessive noise are at increased risk for hearing loss, abnormal brain sensory development, and speech and language problems. Reducing noise levels in the NICU can improve the physiologic stability of sick neonates and therefore enlarge the potential for infant brain development. Apart from the disadvantage of being relatively noisy, the added mechanical parts comprising the known in the art solutions connected to the incubator, enlarge the total volume the incubator encompasses. This is not convenient in many imaging devices, such as magnetic resonance device or CT scanners in which the optimal imaging space is limited, and the precise location of the imaged patient is important for providing optimal images.

It is thus still a long felt need to provide an effective, safe, silent, MRI safe, vented and thermo-regulated neonate's environment, especially when intended for imaging systems.

SUMMARY OF THE INVENTION

The present invention provides a passive neonatal transport incubator (PNTI), useful for thermo-regulating a neonate, comprising an inner volume configured by means of size and shape to accommodate the neonate, the inner volume is defined by an envelope having a main longitudinal axis with a proximal end and an opposite distal end; wherein the envelope is at least partially perforated.

It is another object of the current invention to disclose the PNTI as described above, wherein the PNTI is configured to be ventilated by an independently ventilated medical device.

It is another object of the current invention to disclose the PTI as described above, wherein the medical device is selected from a group consisting of: incubator, cart, magnetic resonance device (MRD), CT scanner, X-ray device, ultrasonography device, elastography, fluoroscopy device, photoacoustic imaging device, thermography device, functional near-infrared spectroscopy, medical photography device and nuclear medicine functional imaging device, positron emission tomography (PET) device, operating table, treatment table, and any combination thereof.

It is another object of the current invention to disclose the PTI as described above, wherein the PNTI is configured by means of size and shape to be inserted into an MRD bore, placed on a patient table of a medical device, placed instead of a patient table of a medical device, or any combination thereof.

It is another object of the current invention to disclose the PTI as described above, wherein at least one of the following holds true: (a) the envelope is permeable in a manner selected from a group consisting of unidirectional, bidirectional and any combination thereof; (b) the perforations are at least partly permeable to ventilation; and, (c) the PNTI is permeable to radiation selected from a group consisting of alpha, beta, gamma, x-ray, magnetic, ionizing, thermal, infrared, sound, and any combination thereof.

It is another object of the current invention to disclose the PTI as described above, additionally comprising air turbulating means (ATM) for slowing and moderating airflow.

It is another object of the current invention to disclose the PTI as described above, wherein at least a portion of the PNTI is made of MRI-safe materials.

It is another object of the current invention to disclose the PTI as described above, wherein at least a portion of the PNTI comprises materials selected from: vibration absorptive materials, sound absorptive materials, liquid resistant materials, fire resistant materials, recyclable materials, disposable materials, at least partially transparent materials, flexible materials or any combination thereof.

It is another object of the current invention to disclose the PTI as described above, wherein at least one of the following holds true: (a) the PNTI comprises at least one port configured for the docking or passage of life support equipment, tubing or both; (b) the PNTI comprises at least one opening for inserting the neonate; (c) the PNTI comprises at least one opening configured to allow entrance of a handler's hand; and, (d) the PNTI additionally comprises a reversibly attachable imperforated layer outside the envelope.

It is another object of the current invention to disclose the PTI as described above, additionally comprising at least one temperature regulating vent (TRV) in fluid communication with the PNTI.

It is another object of the current invention to disclose the PTI as described above, wherein at least one of the following holds true: (a) the TRV is located at at least one of the ends; further wherein the TRV is configured to stream air from the end towards the opposite end substantially along the axis; further wherein the PNTI is configured, by means of size and shape, to accommodate the neonate in parallel to the axis; (b) the TRV is a module selected from a group consisting of at least one first venting module, at least one first heating/cooling module, at least one air filter located adjacently to either the first venting module or the first heating/cooling module and any combination thereof; (c) the TRV comprises at least one venting module configured to introduce air selected from a group consisting of: heated air, cooled air, humidified air, filtered air, room temperature air, predetermined gas concentrated air, and any combination thereof into the PNTI; (d) the TRV comprises a feedback mechanism for the air quality selected from a group consisting of: temperature, humidity, pressure, airborne particle content, gas concentration, and any combination thereof, configured to maintain the quality in a predetermined value or value range; (e) the TRV is a fan, having at least one rotor rotating perpendicularly to a rotor's shaft, and further wherein the shaft is positioned in parallel to the PNTI's main longitudinal axis; (f) the TRV is configured to provide linear air flow, turbulent air flow or both within at least a portion of the PNTI inner volume; (g) the PNTI, the TRV or both comprising sound attenuating means, configured to at least partially attenuate the sound of: the TRV, air movement within the PNTI, sound generated by an MRD, sound external to the PNTI, sound generated by the entrance of air into the PNTI, or any combination thereof; (h) the TRV is comprised of at least one venting module located at: the mobile base, at least one support, at least one PNTI end, or any combination thereof; further wherein the venting module is connected to the PNTI by at least one tubing; (i) the PNTI comprises a central processing unit (CPU); further wherein the CPU is configured to control the TRV, control the TRV by responding to signals received from at least one sensor, control the TRV according to values defined by the user, control the TRV according to predefined physical condition of the neonate, or any combination thereof; and, (j) the TRV is: one first TRV located in one of the ends and at least one second TRV located in the opposite end, at least one TRV is located within the PNTI, at least one TRV is located outside the PNTI and is in fluid communication with the PNTI by means of a tubing; at least one TRV is in fluid communication with the PNTI, or at least one TRV is located remotely from the PNTI.

It is another object of the current invention to disclose the PTI as described above, wherein the PNTI is in air communication with at least one air recycling mechanism (ARM); the ARM comprising: (a) at least one air inlet for collecting air stream from the PNTI's outer environment towards the PNTI's inner environment; and, (b) at least one recycled-air outlet for collecting air streamed from the PNTI's inner environment.

It is another object of the current invention to disclose the PTI as described above, wherein at least one of the following is held true: (a) the PNTI additionally comprising at least one air flow regulator for regulating at least one air stream selected from a group consisting of: recycled air stream, air stream from the PNTI's outer environment, air streamed towards the PNTI's inner environment, and any combination thereof; (b) the PNTI additionally comprises: at least one air baffler, at least one air filter, or any combination thereof; (c) the PNTI is configured to direct the airflow drift to bypass the location of the neonate residing within; and, (d) the PNTI, is in fluid connection to externally supplied pressurized gas. It is another object of the current invention to disclose the PTI as described above, wherein the PNTI is interconnected to an MRI-safe cart.

It is another object of the current invention to disclose the PTI as described above, wherein the PNTI comprises at least one air entry port in connection with: an external venting module, an external humidifier, tubing, external air purifier, external heating/cooling device, external evaporated drug administrating device, or any combination thereof.

It is another object of the current invention to disclose the PTI as described above, wherein at least one of the following is held true: (a) at least one of the perforations is configured to receive a signal and respond by at least partially opening or closing the perforation; (b) at least one of the perforations is adjustable in a manner selected from a group consisting of: size, amount, location, and any combination thereof; (c) at least one of the perforations is at least partially sealable; (d) at least one of the perforations is connected to a maneuverable baffle; (e) at least one of the perforations comprises at least one air filter; (f) at least one of the perforations is configured by means of size and shape to attenuate a predetermined sound; and, (g) at least one of the perforations is configured to direct the airflow drift to bypass the location of the neonate residing within.

It is another object of the current invention to disclose the PTI as described above, wherein the PNTI comprises sound attenuating means configured to at least partially attenuate a selected from: the sound of air flow into the PNTI, the sounds generated by the MRD the sound of air flow within the PNTI, the sounds generated by the external environment, or any combination thereof.

It is another object of the current invention to disclose the PTI as described above, wherein the PNTI comprises at least one sensor selected from a group consisting of: a temperature sensor, a motion sensor, a breathing sensor, a gas concentration sensor, an air flow sensor, a humidity sensor, a door opening or closing sensor, a weight sensor, an RF sensor, an air pressure sensor, a cardiovascular activity sensor, a magnetic field sensor, a radiation sensor, and any combination thereof.

It is another object of the current invention to disclose the PTI as described above, wherein at least one of the following holds true: (a) the PNTI comprises a central processing unit (CPU); (b) the PNTI additionally comprising a CPU configured to control the air flow passing through the perforation in response to a predetermined value of a parameter of the PNTI inner volume selected from a group consisting of: information from at least one sensor, air pressure, temperature, humidity, sound levels, gas concentration, airborne particle count, and any combination thereof.

It is another object of the current invention to disclose the PTI as described above, wherein at least a portion of the PNTI's walls are double jacket walls arrangement (DJW), comprising an inner wall and an outer wall; the DJW comprising at least partly perforated inner-wall and an intact non-perforated outer-wall, or the outer wall and the inner wall are both at least partly perforated, thereby the DJW facilitating the air stream, along the main longitudinal axis in a conduit having a predefined width (w) and length (l).

It is another object of the current invention to disclose the PTI as described above, wherein the conduit between the double jacket walls comprises: sound attenuating means, thermal isolating materials, vibration reducing means, RF coils, conductive material, non-conductive material, or any combination thereof.

It is another object of the current invention to disclose the PTI as described above, wherein at least a portion of the width and the length (w, l) are equal along the longitudinal axis, changes along the longitudinal axis, or any combination thereof.

The present invention provides a method for passively thermo-regulating a neonate, characterized by (a) obtaining a passive neonatal transport incubator (PNTI), useful for thermo regulating a neonate, comprising an envelope defining an inner volume configured by means of size and shape to accommodate the neonate, having a main longitudinal axis with a proximal end and an opposite distal end; the envelope is at least partially perforated; (b) accommodating the neonate in the PNTI; (c) introducing the PNTI in a thermo-regulated environment; and, operating the same.

It is another object of the current invention to disclose the method as described above, additionally comprising the step of ventilating the PNTI to be ventilated by an independently ventilated medical device; the medical device is selected from a group consisting of: incubator, cart, magnetic resonance device (MRD), CT scanner, X-ray device, ultrasonography device, elastography, fluoroscopy device, photoacoustic imaging device, thermography device, functional near-infrared spectroscopy, medical photography device and nuclear medicine functional imaging device, positron emission tomography (PET) device, operating table, treatment table, and any combination thereof.

The present invention provides a standard of care for thermo-regulating a neonate, comprising steps of: (a) obtaining a passive neonatal transport incubator (PNTI), useful for thermo regulating a neonate, comprising an envelope defining an inner volume configured by means of size and shape to accommodate the neonate, having a main longitudinal axis with a proximal end and an opposite distal end; the envelope is at least partially perforated; (b) accommodating the neonate in the PNTI; and, (c) introducing the PNTI into a thermo-regulated environment; wherein the PNTI is thermo regulated at least partially through the perforations; further wherein at least one of the following is held true: (a) the noise level in the PNTI is below 60 Decibels; (b) the noise level in the PNTI is below 45 Decibels; (c) the temperature in the PNTI is at most 2° C. higher or lower from the set temperature; (d) the $CO_2$ concentration within the PNTI does not exceed 4%; (e) the $O_2$ concentration within the PNTI does not fall below 30 vol. %, and does not exceed 40 vol. %; (f) the air velocity over the mattress within the PNTI does not exceed 0.35 m/s; (g) the amount of thermoregulation related complications of neonates when utilizing the PNTI is b times lower than the average value of thermoregulation complications of neonates; b is equal or greater than 1.05; (h) the average value of salivary cortisol level index from noise derived stress of patient when utilizing the PNTI during MRI is n times lower than the average value during MRI; n is equal or greater than 1.05; (i) the average number of MRI repetition number per patient is p times lower when utilizing the PNTI than the average number of MRI repetitions during MRI of patients; p is equal or greater than 1.05; (j) the average value of salivary cortisol level index from open space related stress of patient when utilizing the PNTI during MRI is q times lower than the average the value during MRI; q is equal or greater than 1.05; (k) the PNTI continues to be used safely in occurrence of a leakage of up to 200 ml deposited in the inner volume of the PNTI; (l) the PNTI remains stable when tilted 10° in normal use and when tilted 20° during transportation; (m) the PNTI does not tip over when encountered with a force of 100 N or less; (n) the average number of patients MRI related fall incidents when utilizing the PNTI is r times lower than the average of patients MRI related fall incidents; r is equal or greater than 1.05; (o) the radiated electromagnetic fields in the inner volume of the PNTI, comprising electrical equipment system will be at a level up to 3 V/m for the frequency range of the collateral standard for EMC (electromagnetic compatibility); further the electrical equipment is performing its intended function as specified by the manufacturer or fail without creating a safety harm at a level up to 10 V/m for the frequency range of the collateral standard for EMC; and, (p) the average number of insurable claims of: manufacturer, handler, user, operator, medical care personal, medical facility, medical facility management or any combination thereof when utilizing the PNTI is v times lower than patient MRI associated insurable claims; v is equal or greater than 1.05.

BRIEF DESCRIPTION OF THE FIGURES

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The present invention may be practiced according to the claims without some or all of these specific details. For the purpose of clarity, technical material that is known in the technical fields related to the invention has not been described in detail so that the present invention is not unnecessarily obscured. In the accompanying drawing: In order to understand the invention and to see how it may be implemented in practice, a few preferred embodiments will now be described, by way of non-limiting example only, with reference to be accompanying drawings, in which:

FIG. 10A, illustrating in an out of scale manner an embodiment of the invention, a double jacket PNTI constructed by multiple envelops, creating an air conduit between them;

FIG. 10B, schematically illustrating a cross-section of a portion of the upper (infant's ceiling side) double jacket of the walls (250, 251), width (w) is equal along the conduit (253) providing air inflow and outflow (202B, 202A);

FIG. 10C, schematically illustrating a cross-section portion of the upper (infant's ceiling side) double jacket of the walls (250, 251) of an PNTI in non-limiting and out-of-scale manners; Width is varied in a manner that initial width (w) is narrow and then width increases (W);

FIG. 10D, schematically illustrating a cross-section portion of the upper (infant's ceiling side) the double jacket of the walls (250, 251) of an PNTI in non-limiting and out-of-scale manners; Thermo-regulated air flow (1008) is streamed from the proximal side (101) of the incubator via conduit (253); Width is varied in a manner that initial width (W) decrease along the conduit to a width w;

DETAILED DESCRIPTION OF THE PREFERRED EMBODIMENTS

Figure 1A:
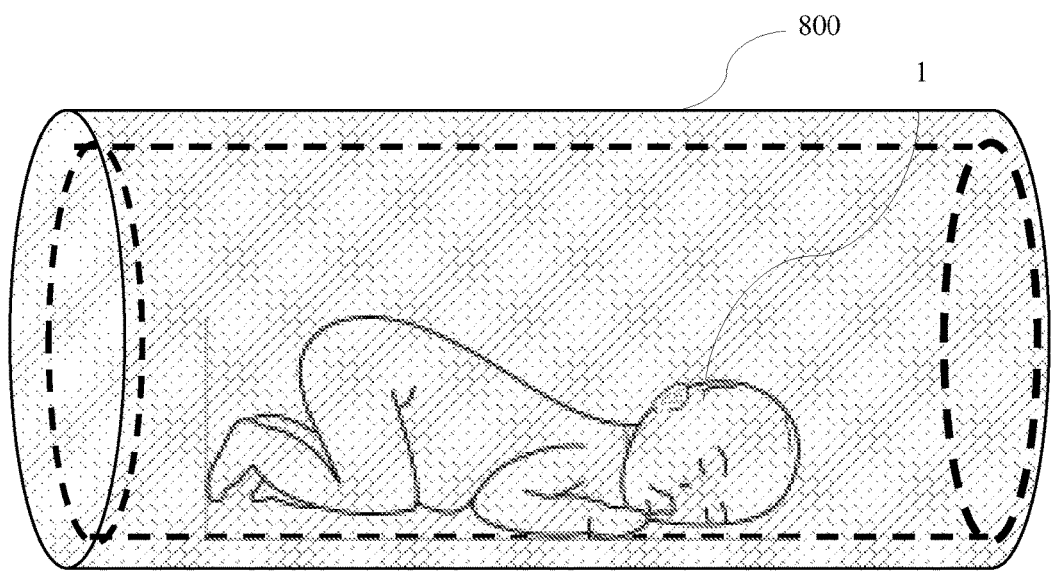
FIG. 1A, illustrating in an out of scale manner a passive neonates transport incubator (PNTI) in a cylindered embodiment.

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The present invention may be practiced according to the claims without some or all of these specific details. For the purpose of clarity, technical material that is known in the technical fields related to the invention has not been described in detail so that the present invention is not unnecessarily obscured.

The essence of the present invention is to provide a passive thermo-regulating neonatal transport incubator and methods thereof.

The term "neonate's accommodating means" refers hereinafter to any means useful for holding a neonate in a position within an incubator in parallel to its longitudinal axis. This position can be in lying, substantially horizontal, position (on his/hers back, stomach, or side), in an at least partially reclining position, or in at least partially sitting position.

The term "thermo-regulated environment" refers hereinafter to an environment that its air temperature is in a constant pre-determined temperature with an error of ±2° C.

The term "along" refers hereinafter to a parallel flow, to a rotational coil-like flow or any combination thereof.

The term "fluid communication" refers hereinafter to a communication between two objects that allow flow of matter (gas, fluid or solid) at least one direction between them.

The term "venting module" refers hereinafter to a module that circulates air and distributes it either evenly or in a defined direction. More specifically the term relates to a fan, a jet, a blower, a compressor, a pump, air streamer, propeller, ventilator, thermantidote, axial-flow fans, centrifugal fan, cross-flow fan, airflow generated using the Coandă effect, etc.

The term "heating/cooling module" refers hereinafter to a module that controls the temperature either by heating or by cooling or by doing both. More specifically the term relates to an air conditioned system, an infrared heater, a water/oil-heated radiator, a coiled heater, an open coil air heater, a round open coil air heater, a convection heater, straight or formed tubular heaters, a quartz tube air heater, a capacitor-type heater, a Pelletier module, etc.

The term "baffle" refers hereinafter to a low-directing or obstructing vanes or panels. More specifically the term relates to longitudinal flow baffles, impingement baffles, orifice baffles, single segmental baffles, double segmental, etc.

The term "air turbulating means" refers hereinafter to any means that controls, softens, moderates and gentles airstream. More specifically the term relates to pre active members, such as fan, multiple-fan arrangement or cascade thereof, air pump, Dyson-type bladeless air multiplier, venting apparatus etc., and/or passive members, such as texturized strainer, curved conduits in a continuous barrier etc.

The term "turbulent flow" refers herein after to the motion of a fluid having local velocities and pressures that fluctuate randomly. The movement of the fluid (e.g. liquid, gas) in characterized by having subcurrents displaying turbulence, moving in irregular patterns, while the overall flow is in one direction. In turbulent flow the speed of the fluid at a point is continuously undergoing changes in both magnitude and direction.

The term "linear flow" refers herein after to laminar flow of a liquids or gases (e.g. air) in a laminar flow, in which the fluid moves in smooth paths or layers. Flow in which turbulence is not exhibited is called laminar.

The term "Venturi effect" refers hereinafter to the reduction in fluid or gas pressure that results when a fluid flows through a constricted section of pipe. The velocity of the fluid or gas increases as the cross sectional area decreases, with the static pressure correspondingly decreasing.

The term "proximal side" refers hereinafter to the side of the longitudinal axis of the PNTI that is adjacent to the head of a neonate placed within.

The term "distal side" refers hereinafter to the side of the longitudinal axis opposite to the proximal side.

The term "neonate" interchangeably refers herein after to a term selected from a group of: neonate, newborn, baby, infant, toddler, child, adolescent, adult, elderly, patient, individual, subject, inmate, sufferer, outpatient, case, client, etc.; further this term refers to person, animal, or sample, as a whole or a portion thereof.

The term "transparent material" interchangeably refers hereinafter to materials such as, poly-methyl methacrylate, thermoplastic polyurethane, polyethylene, polyethylene terephthalate, isophthalic acid modified polyethylene terephthalate, glycol modified polyethylene terephthalate, polypropylene, polystyrene, acrylic, polyacetate, cellulose acetate, polycarbonate, nylon, glass, polyvinyl chloride, etc. Further in some embodiments at least a portion of this material is imbedded with non-transparent materials for means of strength and/or conductivity such as metallic wires.

The term "sensor" interchangeably refers hereinafter to any device that receives a signal or stimulus (heat, pressure, light, motion, sound, humidity etc.) and responds to it in a distinctive manner. This manner can be such as inducing the action/inaction of other devices, inducing the action/inaction of indicators (visual, auditable or sensible), inducing the display of the input received by the sensor, inducing the data storage/analysis of input in a central processing unit, etc.

The term "life supporting equipment" interchangeably refers hereinafter to any element that provides an environmental condition, a medical condition or monitoring of an environmental or medical condition thereof that assists in sustaining the life of a neonate and/or bettering their physical and physiological wellbeing. This element can be: (a) any medical equipment: all devices, tubes, connectors, wires, liquid carriers, needles, sensors, monitors, etc., that are used by medical personal in association with the patient. This equipment is such as bilirubin light, an IV (intravenous) pump, oxygen supplementation systems by head hood or nasal cannula, continuous positive airway pressure system, a feeding tube, an umbilical artery catheter, a fluid transport device, hemofiltration system, hemodialysis system, MRI contras solution injection, imaging the neonate etc.; (b) medical measurement and observation systems (including sensors and/or monitors) of temperature, respiration, cardiac function, oxygenation, brain activity such as ECG (electro-cardiography) monitor, blood pressure monitor, cardio-respiratory monitor, pulse oximeter; and (c) environmental control systems such as ventilator, air conditioner, humidifier, temperature regulator, climate control systems, noise muffling device, vibration muffling device, etc. and any combination thereof.

The term "medical equipment tubing" interchangeably refers hereinafter to all tubes, cables, connectors, wires, liquid carriers, gas carriers, electrical wires, monitoring cables, viewing cables, data cables, etc., that is used in connection to life support equipment, medical equipment or physical environment maintenance or monitoring.

The term "CPU", central processing unit, interchangeably refers hereinafter to the hardware within a computer that carries out the instructions of a computer program by performing the basic arithmetical, logical, and input/output operations of the system. In the embodiments of the invention the CPU can be connected to: a user interface, at least one sensor, at least one indicator, at least one venting module, at least one temperature regulating vent, at least one air filter, at least one sound filter, at least one humidifier, at least one air circulating mechanism, life supporting equipment, a control panel, a monitoring device, a viewing or filming device, and etc., at last one engine configured to convert electrical power into movement of such as a vent, a baffle, a recline-able neonate restraint means, sealing of at least one opening in the incubator, or and etc., thus providing the user monitoring and/or control over various aspects of the invention.

The term 'magnetic resonance imaging device' (MRD), specifically applies hereinafter to any Magnetic Resonance Imaging (MRI) device, any Nuclear Magnetic Resonance (NMR) spectroscope, any Electron Spin Resonance (ESR) spectroscope, any Nuclear Quadruple Resonance (NQR), any Laser magnetic resonance device, any Quantum Rotational field magnetic resonance device (cyclotron), and any combination thereof. The term, in this invention, also applies to any other analyzing and imaging instruments comprising a volume of interest, such as computerized tomography (CT), ultrasound (US) etc. The MRD hereby disclosed is optionally a portable MRI device, such as the ASPECT-MR Ltd commercially available devices, or a commercially available non-portable device. Additionally or alternatively, the MRD is self-fastening cage surrounding a magnetic resonance device as depicted in U.S. Pat. No. 7,719,279 B2, filed 27 May 2008 titled: "SELF-FASTENING CAGE SURROUNDING A MAGNETIC RESONANCE DEVICE AND METHODS THEREOF", of which is hereby incorporated by reference in its entirety.

The term "MRI-safe" interchangeably refers herein to any material that, when used in the MR environment, will present no additional risk to the patient and not significantly affect the quality of the diagnostic information. The material is completely non-magnetic, non-electrically conductive, and non-RF reactive, eliminating all of the primary potential threats during an MRI procedure.

The term "sound attenuation means" interchangeably refers herein to any means configured for attenuating or muffling general and specific sounds, including:
    passive acoustic attenuators such as resonators designed for specific frequencies, sound absorptive materials and linings. Passive sound absorptive materials that are used incorporated with the PNTI, having at least a portion of the sound energy dissipated within the medium itself as sound travels through them can be such as porous materials commonly formed of matted or spun fibers; panel (membrane) absorbers having an impervious surface mounted over an airspace; and resonators created by holes or slots connected to an enclosed volume of trapped air. Common porous absorbers allow air to flow into a cellular structure where sound energy is converted to heat. These may include a thick layer of cloth or carpet, spray-applied cellulose, aerated plaster, fibrous mineral wool and glass fiber, open-cell foam, and felted or cast porous ceiling tile. Thickness plays an important role in sound absorption by porous materials.

Other absorbers are panel absorbers. Typically, panel absorbers are non-rigid, non-porous materials which are placed over an airspace that vibrates in a flexural mode in response to sound pressure exerted by adjacent air molecules for example thin wood paneling over framing, lightweight impervious ceilings and floors, glazing and other large surfaces capable of resonating in response to sound.

The term "resonators" interchangeably refers herein to a structure configured to typically act to absorb sound in a narrow frequency range. Resonators include some perforated materials and materials that have openings (holes and slots). Such as a Helmholtz resonator, which has the shape of a bottle. The resonant frequency is governed by the size of the opening, the length of the neck and the volume of air trapped in the chamber. Typically, perforated materials only absorb the mid-frequency range unless special care is taken in designing the facing to be as acoustically transparent as possible.

active sound controlling devices that create destructive interferences using a secondary source of noise such as using actuator loudspeakers. Some active sound controlling devices use active feedback mechanisms utilizing information received from sound sensors in various locations, and respond to the specific frequency and sound level received. An active sound control mechanism can be efficiently employed in a system with a vent whose generated sound frequency can be calculated.
  hybrid sound attenuating systems that employ both active and passive elements to achieve sound reduction and adaptive-passive systems that use passive devices whose parameters can be varied in order to achieve optimal noise attenuation over a band of operating frequencies, such as a tunable Helmholtz resonator.

As disclosed in the art, for example in "Air transparent soundproof window", arXiv: 1307.0301 [cond-mat.mtrl-sci] arxiv.org/abs/1307.0301, http://phys.org/news/2013-07-materials-scientists-window-mutes-air.html#j-Cp describing a screen that although passable to air, lowers the sound transmitted by up to 35 dB, by designing specific chambers and holes configured to capture and attenuate sound, consisting of a three-dimensional array of diffraction-type resonators with many holes centered at each individual resonator. Further, the researchers note that changing the size of the hole allows for muting different frequencies.

It is further within the scope of the invention a transport incubator having a perforated envelope, comprising a construct with resonators configured to attenuate sound. Additionally or alternatively, the envelope comprises volume having height represented by h, and is measured preferably in millimeters. The value of h can be constant or variable throughout the transport incubator. In at least a portion of this volume resonators and attenuators can be implemented. Further this volume can be filled with sound absorptive material situated around the perforations.

The term "sound shield" refers herein after to any barriers or sound reflection panel, screens, baffle, single or a plurality of, configured to lowering the sound reaching the neonate.

The term "patient table" interchangeably refers herein to any predetermined location provided by a medical device dedicated to placing the examined/treated/imaged/operated patient; such as a countertop, shelf, stretcher, bed, cradle, restraining device, table, recliner, chair, patient placement, or any object designated for placing the patient while being imaged and/or medically treated. In magnetic resonance devices, for example, the location of the patient bed is carefully determined as to be placed optimally in reference to the magnetic field generated by the magnets.

The term "air filter" interchangeably refers herein to any a device configured to remove solid particulates from the air. Typically the filter removes particles of fibrous materials such as dust, pollen, mold, and bacteria from the air, excess humidity, smoke particles, allergens, pet dander, mold spores, dust mite feces, bacteria, viruses, any molecule derived from bacteria, viruses protozoa, animal; any predetermined airborne molecular contaminates such as volatile organic compounds or ozone, etc., and any combination thereof. The filter is such as a chemical filter, air ionisers, oil bath filters air purifier, HEPA filter, and etc. The filter can further employ an air purifying mechanism known in the art, such as passing an electrical current, or static, thermodynamic sterilization system, ultraviolet germicidal irradiation, activated carbon, photocatalytic oxidation electrostatic precipitators, titanium dioxide ($TiO_2$) technology, and etc.

The term "patient placement" interchangeably refers herein to any location within the inner volume of the PNTI configured to accept a patient, e.g. neonate. Additionally or alternatively, this location can comprise a bed, a restraint, a mattress, concave shape, pillow, ergonomic shape, belts, straps, flat surface, at least partially flexible surface, a disposable portion, a sterilizable portion, confinement means, and any combination thereof.

The term "plurality" interchangeably refers herein to one and/or more than one.

The term "cart" refers hereinafter to any apparatus used for transporting the cart. This includes any transport device or any small vehicle pushed or pulled by manually, automatically or both. More specifically the term relates to a structure able to hold the incubator having mobility providing elements such as one or a plurality of a wheel, roller, sliding blade, rotating belt, etc. For example, trolley, handcart, pushcart, electric cart, wagon, barrow, rickshaw, ruck, wagon, barrow, buggy, dolly, carriage, float, cab, dray, gig, gurney, handcart, palanquin, pushcart, tumbrel, wheelbarrow, curricle, etc.

According to one embodiment of the invention a passive thermo-regulated neonatal transport incubator (PNTI), comprising an envelope surrounding an inner volume configured by means of size and shape to accommodate the neonate, having a main longitudinal axis with a proximal end and an opposite distal end; wherein the envelope is at least partially perforated.

According to another embodiment of the invention, a PNTI as defined above is disclosed, wherein the PNTI is configured to be ventilated by an independent ventilating medical device; the medical device is selected from a group consisting of: incubator, cart, magnetic resonance device (MRD), CT scanner, X-ray device, ultrasonography device, elastography, fluoroscopy device, photoacoustic imaging device, thermography device, functional near-infrared spectroscopy, medical photography device and nuclear medicine functional imaging device, positron emission tomography (PET) device, operating table, treatment table, and any combination thereof.

According to another embodiment of the invention, a PNTI as defined above is disclosed, wherein the PNTI is configured by means of size and shape to be inserted into an MRD bore.

According to another embodiment of the invention, a PNTI as defined above is disclosed, wherein the envelope is permeable in a manner selected from a group consisting of unidirectional, bidirectional and any combination thereof.

According to another embodiment of the invention, a PNTI as defined above is disclosed, wherein the PNTI is permeable to radiation selected from a group consisting of alpha, beta, gamma, x-ray, magnetic, ionizing, thermal, infrared, sound, and any combination thereof.

According to another embodiment of the invention, a PNTI as defined above is disclosed, wherein the PNTI comprises at least one folded configuration and one unfolded configuration.

According to another embodiment of the invention, a PNTI as defined above is disclosed, wherein the folded configuration is configured for storing the PNTI with minimum volume uptake.

According to another embodiment of the invention, a PNTI as defined above is disclosed, additionally comprising air turbulating means (ATM) for slowing and moderating airflow.

According to another embodiment of the invention, a PNTI as defined above is disclosed, wherein at least a portion of the PNTI is made of MRI-safe materials.

According to another embodiment of the invention, a PNTI as defined above is disclosed, wherein at least a portion of the PNTI comprises materials selected from a group consisting of: vibration absorptive, sound absorptive, liquid resistant, fire resistant, recyclable materials, disposable materials, flexible materials, at least partially transparent materials, and any combination thereof.

According to another embodiment of the invention, a PNTI as defined above is disclosed, wherein the PNTI comprises at least one movable hinge segment.

According to another embodiment of the invention, a PNTI as defined above is disclosed, wherein the PNTI comprises at least one port configured for the docking or passage of life support equipment, tubing or both.

According to another embodiment of the invention, a PNTI as defined above is disclosed, wherein the envelope comprises at least one opening for inserting the neonate.

According to another embodiment of the invention, a PNTI as defined above is disclosed, wherein the PNTI comprises at least one reversibly connected patient placement.

According to another embodiment of the invention, a PNTI as defined above is disclosed, wherein the PNTI is of a shape selected from a group consisting of polygonal, round, symmetrical, non-symmetrical and any combination thereof.

According to another embodiment of the invention, a PNTI as defined above is disclosed, additionally comprising at least one temperature regulating vent (TRV) in fluid communication with the PNTI.

According to another embodiment of the invention, a PNTI as defined above is disclosed, wherein the TRV is located at least one of the ends; further wherein the TRV is configured to stream air from the end towards the opposite end substantially along the axis; further wherein the PNTI is configured, by means of size and shape, to accommodate the neonate in parallel to the axis.

According to another embodiment of the invention, a PNTI as defined above is disclosed, wherein the TRV is a module selected from a group consisting of at least one first venting module, at least one first heating/cooling module, at least one filter located adjacently to either the first venting module or the first heating/cooling module and any combination thereof.

According to another embodiment of the invention, a PNTI as defined above is disclosed, wherein the TRV comprises at least one venting module configured to introduce air selected from a group consisting of: heated air, cooled air, humidified air, filtered air, room temperature air, predetermined gas concentrated air, and any combination thereof into the PNTI.

According to another embodiment of the invention, a PNTI as defined above is disclosed, wherein the TRV comprises a feedback mechanism for the air quality selected from a group consisting of: temperature, humidity, pressure, airborne particle content, gas concentration, and any combination thereof, configured to maintain the quality in a predetermined value or value range.

According to another embodiment of the invention, a PNTI as defined above is disclosed, wherein the TRV is a fan, having at least one rotor rotating perpendicularly to a rotor's shaft, and further wherein the shaft is positioned in parallel to the PNTI's main longitudinal axis.

According to another embodiment of the invention, a PNTI as defined above is disclosed, wherein the TRV is configured to provide an air flow of X per volume W and time Y.

According to another embodiment of the invention, a PNTI as defined above is disclosed, wherein the air flow parameters of X, W, and Y are configurable by the user.

According to another embodiment of the invention, a PNTI as defined above is disclosed, wherein the TRV is configured to provide linear air flow, turbulent air flow or both within at least a portion of the ANTI inner volume.

According to another embodiment of the invention, a PNTI as defined above is disclosed, wherein the PNTI, the TRV or both comprising sound attenuating means, configured to at least partially attenuate the sound of: the TRV, air movement within the PNTI, sound generated by an MRD, sound external to the PNTI, sound generated by the entrance of air into the PNTI, or any combination thereof.

According to another embodiment of the invention, a PNTI as defined above is disclosed, wherein the PNTI is connected to the TRV by flexible vibration absorptive materials, connectors or both.

According to another embodiment of the invention, a PNTI as defined above is disclosed, wherein the PNTI comprises a central processing unit (CPU); further wherein the CPU is configured to control: the TRV, control the TRV by responding to signals received from at least one sensor, control the TRV according to values defined by the user, control the TRV according to predefined physical condition of the neonate, or any combination thereof.

According to another embodiment of the invention, a PNTI as defined above is disclosed, wherein at least one of the following is held true: (a) the PNTI comprising at least one first TRV located in one of the ends and at least one second TRV located in the opposite end; (b) at least one TRV is located within the PNTI; (c) at least one TRV is located outside the PNTI and is in air communication with the PNTI by means of a tubing; and, (d) at least one TRV is in air communication with the PNTI, and at least one TRV is located remotely from the PNTI.

According to another embodiment of the invention, a PNTI as defined above is disclosed, wherein the PNTI is in air communication with at least one air recycling mechanism (ARM); the ARM comprising: (a) at least one air inlet for collecting air stream from the PNTI's outer environment towards the PNTI's inner environment; and, (b) at least one recycled-air outlet for collecting air streamed from the PNTI's inner environment.

According to another embodiment of the invention, a PNTI as defined above is disclosed, additionally comprising at least one air flow regulator for regulating at least one air stream selected from a group consisting of: recycled air stream, air stream from the PNTI's outer environment, air streamed towards the PNTI's inner environment, and any combination thereof.

According to another embodiment of the invention, a PNTI as defined above is disclosed, additionally comprising at least one air baffler.

According to another embodiment of the invention, a PNTI as defined above is disclosed, wherein the PNTI comprises at least one air filter.

According to another embodiment of the invention, a PNTI as defined above is disclosed, wherein the PNTI is configured to direct the airflow drift to bypass the location of the neonate residing within.

According to another embodiment of the invention, a PNTI as defined above is disclosed, wherein the PNTI, is in fluid connection to externally supplied pressurized gas.

According to another embodiment of the invention, a PNTI as defined above is disclosed, wherein at least a portion of the PNTI's walls are double jacket walls arrangement (DJW); the DJW comprising a perforated inner-wall and an intact non-perforated outer-wall, thereby the DJW facilitating the air stream, along the main longitudinal axis in a conduit having a predefined width (w) and length (l).

According to another embodiment of the invention, a PNTI as defined above is disclosed, additionally comprising the PNTI comprising a double jacket wall arrangement; the outer wall and inner wall are both at least partly perforated. Additionally or alternatively, the conduit between the double jacket walls is at least partially filled with noise absorptive materials. Additionally or alternatively, the conduit comprises sound attenuating means.

According to another embodiment of the invention, a PNTI as defined above is disclosed, wherein at least a portion of the width and the length (w, l) are are equal along the longitudinal axis, changes along the longitudinal axis, or any combination thereof.

According to another embodiment of the invention, a PNTI as defined above is disclosed, wherein the PNTI is interconnected to an MRI-safe cart.

According to another embodiment of the invention, a PNTI as defined above is disclosed, wherein the cart in connection with the PNTI is configured to be at least partially inserted within an MRD bore.

According to another embodiment of the invention, a PNTI as defined above is disclosed, wherein the TRV is comprised of at least one venting module located at a selected from a group consisting of: the mobile base, at least one support, at least one PNTI end, and any combination thereof; further wherein the venting module is connected to the PNTI by at least one tubing.

According to another embodiment of the invention, a PNTI as defined above is disclosed, wherein the PNTI comprises at least one air entry port in connection with: an external venting module, an external humidifier, tubing, external air purifier, external heating/cooling device, external evaporated drug administrating device, or any combination thereof.

According to another embodiment of the invention, a PNTI as defined above is disclosed, wherein at least one of the perforations is made of shape memory polymers, configured to have at least one first opened configured shape, and at least one at least partially closed configured shape; further the shape change of the polymer is triggered by: magnetic field, temperature, pH shift, electrical current, electric field, humidity, light, exposure to another substance, pressure stress, or any combination thereof.

According to another embodiment of the invention, a PNTI as defined above is disclosed, wherein at least one of the perforations is configured to receive a signal and at least partially open or close the perforation.

According to another embodiment of the invention, a PNTI as defined above is disclosed, wherein at least one of the perforations is adjustable in a manner selected from a group consisting of: size, amount, location, and any combination thereof.

According to another embodiment of the invention, a PNTI as defined above is disclosed, additionally comprising a reversibly attachable imperforated layer outside the envelope.

According to another embodiment of the invention, a PNTI as defined above is disclosed, wherein at least one of the perforations is at least partially sealable.

According to another embodiment of the invention, a PNTI as defined above is disclosed, wherein at least one of the perforations is permeable in a manner selected from a group consisting of unidirectional, bidirectional and any combination thereof.

According to another embodiment of the invention, a PNTI as defined above is disclosed, wherein at least one of the perforations is connected to a maneuverable baffle.

According to another embodiment of the invention, a PNTI as defined above is disclosed, wherein at least one of the perforations comprise at least one air filter.

According to another embodiment of the invention, a PNTI as defined above is disclosed, wherein at least one of the perforations is of a shape selected from a group consisting of: polygonal, round, symmetrical, non-symmetrical and any combination thereof.

According to another embodiment of the invention, a PNTI as defined above is disclosed, wherein the perforation selected from a group consisting of: equal in size, equal in depth, equal in shape, not equal in size, equal in depth, equal in shape, and any combination thereof.

According to another embodiment of the invention, a PNTI as defined above is disclosed, wherein at least one of the perforations is configured to have smooth edges.

According to another embodiment of the invention, a PNTI as defined above is disclosed, wherein at least one of the perforations is configured to direct the airflow drift to bypass the location of the neonate residing within.

According to another embodiment of the invention, a PNTI as defined above is disclosed, wherein at least one perforations is configured to allow an air flow of X per volume W and time Y, predetermined by the user.

According to another embodiment of the invention, a PNTI as defined above is disclosed, wherein at least a portion of the PNTI is made of noise proof materials.

According to another embodiment of the invention, a PNTI as defined above is disclosed, wherein the PNTI comprises sound attenuating means configured to at least partially attenuate: the sound of air flow into the PNTI, the sounds generated by the MRD the sound of air flow within the PNTI, the sounds generated by the external environment, or any combination thereof.

According to another embodiment of the invention, a PNTI as defined above is disclosed, wherein at least one of the perforations is configured by means of size and shape to attenuate a predetermined sound.

According to another embodiment of the invention, a PNTI as defined above is disclosed, wherein the PNTI is constructed of a plurality of layers.

According to another embodiment of the invention, a PNTI as defined above is disclosed, at least one of the layers comprises materials selected from a group consisting of: vibration absorptive, sound absorptive, liquid resistant, fire resistant, recyclable material, disposable material, sterilizable material, and any combination thereof.

According to another embodiment of the invention, a PNTI as defined above is disclosed, wherein each of the layers comprises perforations.

According to another embodiment of the invention, a PNTI as defined above is disclosed, wherein the PNTI comprises at least one resonator configured to reflect the sound waves so as to cancel out frequencies generated by the air flow and/or vent.

According to another embodiment of the invention, a PNTI as defined above is disclosed, wherein the PNTI comprises at least one sensor selected from a group consisting of: a temperature sensor, a motion sensor, a breathing sensor, a gas concentration sensor, an air flow sensor, a humidity sensor, a door opening or closing sensor, a weight sensor, an RF sensor, an air pressure sensor, a cardiovascular activity sensor, a magnetic field sensor, a radiation sensor, and any combination thereof.

According to another embodiment of the invention, a PNTI as defined above is disclosed, wherein the sensors are configured to relay sensed information to a CPU, an indicator, or both.

According to another embodiment of the invention, a PNTI as defined above is disclosed, wherein the PNTI comprises a central processing unit (CPU).

According to another embodiment of the invention, a PNTI as defined above is disclosed, wherein the CPU is connected to a user interface selected from a group consisting of: a screen, a touch screen, a joystick, a keyboard, a smartphone, a tablet, a motion detector, control panel, buttons, and etc. further any data from the PNTI can be transmitted to the internet, sms, pager, E-mail, RF signal, by any short range communication such as blue tooth, and etc., and any long range communication such as RF.

According to another embodiment of the invention a PNTI as described above is disclosed, wherein the PNTI additionally comprises viewing equipment configured to enable viewing of the housed neonate and transmit this information by wire or wirelessly.

According to another embodiment of the invention, a PNTI as defined above is disclosed, wherein the CPU is configured to control the air flow passing through the perforation in response to a predetermined value of a parameter of the PNTI inner volume selected from a group consisting of: information from at least one sensor, air pressure, temperature, humidity, sound levels, gas concentration, airborne particle count, and any combination thereof.

According to another embodiment of the invention, a PNTI as defined above is disclosed, wherein the CPU is configured to control the perforation characteristic selected from a group consisting of: size, permeability, amount location and any combination thereof, by responding to signals received from the sensors.

According to another embodiment of the invention, a PNTI as defined above is disclosed, wherein at least one of the perforations is configurable by means selected from a group consisting of opening angle, maneuvering an attached baffle, perforations location, maneuvering a shutter, closing or opening at least one of the perforations and any combination thereof, to direct the airflow to bypass the location of the neonate residing within.

According to another embodiment of the invention, a PNTI as defined above is disclosed, wherein the PNTI comprises vibration absorptive materials, connections or both.

According to another embodiment of the invention, a PNTI as defined above is disclosed, wherein at least a portion of the PNTI comprises texture configured to attenuate sound, to minimize movement of the PNTI, to ease grasp of PNTI, or any combination thereof.

According to another embodiment of the invention, a PNTI as defined above is disclosed, wherein the PNTI is connected to life supporting equipment.

According to another embodiment of the invention, a PNTI as defined above is disclosed, wherein the PNTI comprises at least one opening configured by means of size and shape for the entrance of the handler's hand into the incubator.

According to another embodiment of the invention, a PNTI as defined above is disclosed, wherein the PNTI comprises connections to a power source: external, internal or both.

According to one embodiment of the invention, a method for passively thermo-regulating a neonate, characterized by (a) obtaining a passive thermo-regulated neonatal transport incubator (PNTI), comprising an envelope surrounding an inner volume configured by means of size and shape to accommodate the neonate, having a main longitudinal axis with a proximal end and an opposite distal end; the envelope is at least partially perforated (b) accommodating the neonate in the PNTI; (c) placing the PNTI in a thermo-regulated environment; and, (d) operating the same.

According to another embodiment of the invention, a method as defined above is disclosed, additionally comprising the step of ventilating the PNTI to be ventilated by an independent ventilating medical device; the medical device is selected from a group consisting of: incubator, cart, magnetic resonance device (MRD), CT scanner, X-ray device, ultrasonography device, elastography, fluoroscopy device, photoacoustic imaging device, thermography device, functional near-infrared spectroscopy, medical photography device and nuclear medicine functional imaging device, positron emission tomography (PET) device, operating table, treatment table and any combination thereof.

According to another embodiment of the invention, a method as defined above is disclosed, additionally comprising the step of selecting the PNTI configured by means of size and shape to be inserted into an MRD bore.

According to another embodiment of the invention, a method as defined above is disclosed, additionally comprising the step of selecting the envelope permeable in a manner selected from a group consisting of unidirectional, bidirectional and any combination thereof.

According to another embodiment of the invention, a method as defined above is disclosed, additionally comprising the step of selecting the PNTI permeable to radiation selected from a group consisting of alpha, beta, gamma, x-ray, magnetic, ionizing, thermal, infrared, sound, and any combination thereof.

According to another embodiment of the invention, a method as defined above is disclosed, additionally comprising the step of the PNTI comprising at least one folded configuration and one unfolded configuration; further comprising the step of at least partially folding or unfolding the PNTI.

According to another embodiment of the invention, a method as defined above is disclosed, additionally comprising the step of folding the PNTI, thereby storing the PNTI with minimum volume uptake.

According to another embodiment of the invention, a method as defined above is disclosed, additionally comprising the step of connecting and/or operating air turbulating means (ATM), thereby slowing and moderating airflow.

According to another embodiment of the invention, a method as defined above is disclosed, additionally comprising the step of selecting the PNTI in which at least a portion of the PNTI is made of MRI-safe materials.

According to another embodiment of the invention, a method as defined above is disclosed, additionally comprising the step of selecting the PNTI in which at least a portion of the ANTI comprises materials selected from a group consisting of: flexible materials, at least partially transparent materials, vibration absorptive, sound absorptive, liquid resistant, fire resistant, recyclable materials, disposable materials, and any combination thereof.

According to another embodiment of the invention, a method as defined above is disclosed, additionally comprising the step of the selecting the PNTI comprising at least one maneuverable hinged segment; further comprising the step of maneuvering the hinged segment.

According to another embodiment of the invention, a method as defined above is disclosed, additionally comprising the step of selecting the PNTI comprising at least one port and docking or passing through a selected from a group consisting of: life support equipment, tubing, and any combination thereof.

According to another embodiment of the invention, a method as defined above is disclosed, additionally comprising the step of selecting the envelope comprising at least one opening for inserting the neonate, and introducing the neonate into the PNTI through the opening.

According to another embodiment of the invention, a method as defined above is disclosed, additionally comprising the step of reversibly connecting at least one patient placement to the PNTI.

According to another embodiment of the invention, a method as defined above is disclosed, additionally comprising the step of selecting the PNTI of a shape selected from a group consisting of polygonal, round, symmetrical, non-symmetrical and any combination thereof.

According to another embodiment of the invention, a method as defined above is disclosed, additionally comprising at least one temperature regulating vent (TRV) in fluid communication with the PNTI.

According to another embodiment of the invention, a method as defined above is disclosed, additionally comprising the steps of: (a) connecting the TRV in at least one of the ends; and, (b) configuring the TRV to stream air from the end towards the opposite end substantially along the axis; wherein the PNTI is configured, by means of size and shape, to accommodate the neonate in parallel to the axis, thereby streaming air in parallel to the neonate.

According to another embodiment of the invention, a method as defined above is disclosed, additionally comprising the step of selecting the TRV module from a group consisting of at least one first venting module, at least one first heating/cooling module, at least one filter located adjacently to either the first venting module or the first heating/cooling module and any combination thereof.

According to another embodiment of the invention, a method as defined above is disclosed, additionally comprising the step of configuring at least one TRV venting module to introduce air selected from a group consisting of: heated air, cooled air, humidified air, filtered air, room temperature air, predetermined gas concentrated air, and any combination thereof, into the PNTI.

According to another embodiment of the invention, a method as defined above is disclosed, additionally comprising the step of operating the TRV feedback mechanism for the air quality selected from a group consisting of: temperature, humidity, pressure, airborne particle content, gas concentration, and any combination thereof; further comprising the step of configuring the TRV to maintain the quality in response to the feedback mechanism in a predetermined value or value range.

According to another embodiment of the invention, a method as defined above is disclosed, additionally comprising the step of selecting the TRV configured as a fan, having at least one rotor rotating perpendicularly to a rotor's shaft, and further wherein the shaft is positioned in parallel to the PNTI's main longitudinal axis.

According to another embodiment of the invention, a method as defined above is disclosed, additionally comprising the step of configuring the TRV to provide an air flow of X per volume W and time Y.

According to another embodiment of the invention, a method as defined above is disclosed, additionally comprising the step of configuring the air flow parameters of X, W, and Y by the user.

According to another embodiment of the invention, a method as defined above is disclosed, additionally comprising the step of configuring the TRV to provide linear air flow, turbulent air flow or both within at least a portion of the PNTI inner volume.

According to another embodiment of the invention, a method as defined above is disclosed, additionally comprising the step of selecting the PNTI the TRV or both comprising sound attenuating means, and configuring the means to at least partially attenuate the sound of a selected from a group consisting of: the TRV, air movement within the PNTI, sound generated by an MRD, sound external to the PNTI, sound generated by the entrance of air into the PNTI, and any combination thereof.

According to another embodiment of the invention, a method as defined above is disclosed, additionally comprising the step of connecting the PNTI to the TRV by flexible vibration absorptive materials, connectors or both.

According to another embodiment of the invention, a method as defined above is disclosed, additionally comprising the step of selecting the PNTI comprising a central processing unit (CPU); further comprising the step of configuring the CPU to control a selected from a group consisting of: the TRV, control the TRV by responding to signals received from at least one sensor, control the TRV according to values defined by the user, control the TRV according to predefined physical condition of the neonate, and any combination thereof.

According to another embodiment of the invention, a method as defined above is disclosed, additionally comprising the step of selecting the PNTI comprising at least one first TRV located at a selected from a group consisting of: in one of the ends and at least one second TRV located in the opposite end, within the PNTI, outside the PNTI, outside the PNTI and air communicating by means of tubing, remotely from the PNTI, remotely from the PNTI and air communicating by means of tubing, and any combination thereof.

According to another embodiment of the invention, a method as defined above is disclosed, additionally comprising the step of air communicating the PNTI with at least one air recycling mechanism (ARM); the ARM comprising: (a) at least one air inlet for collecting air stream from the PNTI's outer environment towards the PNTI's inner environment; and, (b) at least one recycled-air outlet for collecting air streamed from the PNTI's inner environment.

According to another embodiment of the invention, a method as defined above is disclosed, additionally comprising the step of, additionally comprising at least one air flow regulator for regulating at least one air stream selected from a group consisting of: recycled air stream, air stream from the PNTI's outer environment, air streamed towards the PNTI's inner environment, and any combination thereof.

According to another embodiment of the invention, a method as defined above is disclosed, the PNTI, additionally comprising at least one air baffler.

According to another embodiment of the invention, a method as defined above is disclosed, the PNTI additionally comprises at least one air filter.

According to another embodiment of the invention, a method as defined above is disclosed, additionally comprising the step of configuring the PNTI to direct the airflow drift to bypass the location of the neonate residing within.

According to another embodiment of the invention, a method as defined above is disclosed, additionally comprising the step of connecting the PNTI by a fluid connection to externally supplied pressurized gas.

According to another embodiment of the invention, a method as defined above is disclosed, at least a portion of the PNTI additionally comprising double jacket walls arrangement (DJW); the DJW comprising a perforated inner-wall and an intact non-perforated outer-wall, thereby the DJW facilitating the air stream, along the main longitudinal axis in a conduit having a predefined width (w) and length (l).

According to another embodiment of the invention, a method as defined above is disclosed, additionally comprising a step of ventilating and at least partially sound attenuating the inner volume of the PNTI by selecting the PNTI comprising a double jacket wall arrangement; the outer wall and inner wall are both at least partly perforated. Additionally or alternatively, the conduit between the double jacket walls is at least partially filled with noise absorptive materials. Additionally or alternatively, the conduit comprises sound attenuating means.

According to another embodiment of the invention, a method as defined above is disclosed, additionally comprising a step of selecting the PNTI having at least a portion of the width and the length (w, l) are equal along the longitudinal axis, changes along the longitudinal axis, or any combination thereof.

According to another embodiment of the invention, a method as defined above is disclosed, additionally comprising the step of interconnecting the PNTI to an MRI-safe cart.

According to another embodiment of the invention, a method as defined above is disclosed, additionally comprising the step of configuring the cart in connection with the PNTI to be at least partially inserted within an MRD bore.

According to another embodiment of the invention, a method as defined above is disclosed, additionally comprising the step of selecting at least one venting module, of the TRV, located at the mobile base, at least one support, at least one PNTI end, or any combination thereof; further wherein the venting module is connected to the PNTI by at least one tubing.

According to another embodiment of the invention, a method as defined above is disclosed, additionally comprising the step of selecting the PNTI's comprising at least one air entry port and connecting the entry from a group consisting of: an external venting module, an external humidifier, tubing, external air purifier, external heating/cooling device, external evaporated drug administrating device, and any combination thereof.

According to another embodiment of the invention, a method as defined above is disclosed, additionally comprising the step of selecting the PNTI with at least one of the perforations is made of shape memory polymers, and configuring the perforations to have at least one first opened configured shape, and at least one at least partially closed configured shape; further comprising the step of triggering the shape change of the polymer by: magnetic field, temperature, pH shift, electrical current, electric field, humidity, light, exposure to another substance, pressure stress, or any combination thereof, thereby at least partly opening or closing the perforation.

According to another embodiment of the invention, a method as defined above is disclosed, additionally comprising the step of configuring at least one of the perforations to receive a signal and at least partially open or close the perforation.

According to another embodiment of the invention, a method as defined above is disclosed, additionally comprising the step of adjusting at least one of the perforations in a manner selected from a group consisting of: size, amount, location, and any combination thereof.

According to another embodiment of the invention, a method as defined above is disclosed, additionally comprising the step of reversibly attaching an imperforated layer outside the envelope.

According to another embodiment of the invention, a method as defined above is disclosed, additionally comprising the step of at least partially sealing at least one of the perforations.

According to another embodiment of the invention, a method as defined above is disclosed, additionally comprising the step of selecting the perforation permeable in a manner selected from a group consisting of unidirectional, bidirectional and any combination thereof.

According to another embodiment of the invention, a method as defined above is disclosed, additionally comprising the step of maneuvering a baffle connected to at least one of the perforations.

According to another embodiment of the invention, a method as defined above is disclosed, additionally comprising the step of connecting at least one air filter to at least one perforation.

According to another embodiment of the invention, a method as defined above is disclosed, additionally comprising the step of selecting the PNTI having at least one of the perforations of a shape selected from a group consisting of: polygonal, round, symmetrical, non-symmetrical and any combination thereof.

According to another embodiment of the invention, a method as defined above is disclosed, additionally comprising the step of selecting the perforations from a group consisting of: equal in size, equal in depth, equal in shape, not equal in size, equal in depth, equal in shape, and any combination thereof.

According to another embodiment of the invention, a method as defined above is disclosed, additionally comprising the step of configuring at least one of the perforations to have smooth edges.

According to another embodiment of the invention, a method as defined above is disclosed, additionally comprising the step of configuring at least one of the perforations to direct the airflow drift to bypass the location of the neonate residing within.

According to another embodiment of the invention, a method as defined above is disclosed, additionally comprising the step of configuring at least one of the perforations to allow an air flow of X per volume W and time Y, predetermined by the user.

According to another embodiment of the invention, a method as defined above is disclosed, additionally comprising the step of selecting the PNTI, at least a portion of is made of noise proof materials.

According to another embodiment of the invention, a method as defined above is disclosed, additionally comprising the step of the PNTI comprises sound attenuating means configured to at least partially attenuate: the sound of air flow into the PNTI, the sounds generated by the MRD the sound of air flow within the PNTI, the sounds generated by the external environment, or any combination thereof.

According to another embodiment of the invention, a method as defined above is disclosed, additionally comprising the step of selecting the PNTI comprising the perforations, and configuring at least one of the perforations by means of size and shape to attenuate a predetermined sound, and attenuating a predetermined sound.

According to another embodiment of the invention, a method as defined above is disclosed, additionally comprising the step of selecting the PNTI constructed of a plurality of layers.

According to another embodiment of the invention, a method as defined above is disclosed, additionally comprising the step of selecting at least one of the layer's materials from a group consisting of: vibration absorptive, sound absorptive, liquid resistant, fire resistant, recyclable material, disposable material, sterilizable material, and any combination thereof.

According to another embodiment of the invention, a method as defined above is disclosed, additionally comprising the step of selecting at least one layer, at least a portion thereof comprising perforations.

According to another embodiment of the invention, a method as defined above is disclosed, additionally comprising the step of selecting the PNTI additionally comprising at least one sensor selected from a group consisting of: a temperature sensor, a motion sensor, a breathing sensor, a gas concentration sensor, an air flow sensor, a humidity sensor, a door opening or closing sensor, a weight sensor, an RF sensor, an air pressure sensor, a cardiovascular activity sensor, a magnetic field sensor, a radiation sensor, and any combination thereof.

According to another embodiment of the invention, a method as defined above is disclosed, additionally comprising the step of configuring the sensors to relay sensed information to a CPU, an indicator, or both.

According to another embodiment of the invention, a method as defined above is disclosed, additionally comprising the step of connecting central processing unit (CPU) to the PNTI.

According to another embodiment of the invention, a method as defined above is disclosed, additionally comprising the step of configuring the CPU to control the air flow passing through the perforation in response to a predetermined value of a parameter of the PNTI inner volume selected from a group consisting of: information from at least one sensor, air pressure, temperature, humidity, sound levels, gas concentration, airborne particle count, and any combination thereof.

According to another embodiment of the invention, a method as defined above is disclosed, additionally comprising the step of configuring the CPU to control the perforation characteristic selected from a group consisting of: size, permeability, amount location and any combination thereof, by responding to signals received from the sensors.

According to another embodiment of the invention, a method as defined above is disclosed, additionally comprising the step of configuring the perforations by means selected from a group consisting of opening angle, maneuvering an attached baffle, perforations location, maneuvering a shutter, closing or opening at least one of the perforations and any combination thereof, to direct the airflow to bypass the location of the neonate residing within.

According to another embodiment of the invention, a method as defined above is disclosed, the PNTI additionally comprising vibration absorptive materials connections or both.

According to another embodiment of the invention, a method as defined above is disclosed, additionally comprising the step of selecting the PNTI comprising at least a portion of textured exterior, configured to a selected from a group consisting of: to attenuate sound, to minimize movement of the PNTI, to ease grasp of PNTI, and any combination thereof.

According to another embodiment of the invention, a method as defined above is disclosed, additionally comprising the step of connecting the PNTI to life supporting equipment.

According to another embodiment of the invention, a method as defined above is disclosed, additionally comprising the step of inserting a handlers hand into at least one opening in the PNTI, thereby handling the neonate.

According to another embodiment of the invention, a method as defined above is disclosed additionally comprising a step of connecting the PNTI to a power source, internal, external or both.

The present invention provides a standard of care for thermo-regulating a neonate, comprising steps of: (a) obtaining a passive neonatal transport incubator (PNTI), useful for thermo regulating a neonate, comprising an envelope defining an inner volume configured by means of size and shape to accommodate the neonate, having a main longitudinal axis with a proximal end and an opposite distal end; the envelope is at least partially perforated; (b) accommodating the neonate in the PNTI; and, (c) introducing the PNTI into a thermo-regulated environment; wherein the PNTI is thermo regulated at least partially through the perforations; further wherein at least one of the following is held true: (a) the noise level in the PNTI is below 60 Decibels; (b) the noise level in the PNTI is below 45 Decibels; (c) the temperature in the PNTI is at most 2° C. higher or lower from the set temperature; (d) the $CO_2$ concentration within the PNTI does not exceed 4%; (e) the $O_2$ concentration within the PNTI does not fall below 30 vol. %, and does not exceed 40 vol. %; (f) the air velocity over the mattress within the PNTI does not exceed 0.35 m/s; (g) the amount of thermoregulation related complications of neonates when utilizing the PNTI is b times lower than the average value of thermoregulation complications of neonates; b is equal or greater than 1.05; (h) the average value of salivary cortisol level index from noise derived stress of patient when utilizing the PNTI during MRI is n times lower than the average value during MRI; n is equal or greater than 1.05; (i) the average number of MRI repetition number per patient is p times lower when utilizing the PNTI than the average number of MRI repetitions during MRI of patients; p is equal or greater than 1.05; (j) the average value of salivary cortisol level index from open space related stress of patient when utilizing the PNTI during MRI is q times lower than the average the value during MRI; q is equal or greater than 1.05; (k) the PNTI continues to be used safely in occurrence of a leakage of up to 200 ml deposited in the inner volume of the PNTI; (l) the PNTI remains stable when tilted 10° in normal use and when tilted 20° during transportation; (m) the PNTI does not tip over when encountered with a force of 100 N or less; (n) the average number of patients MRI related fall incidents when utilizing the PNTI is r times lower than the average of patients MRI related fall incidents; r is equal or greater than 1.05; (o) the radiated electromagnetic fields in the inner volume of the PNTI, comprising electrical equipment system will be at a level up to 3 V/m for the frequency range of the collateral standard for EMC (electromagnetic compatibility); further the electrical equipment is performing its intended function as specified by the manufacturer or fail without creating a safety harm at a level up to 10 V/m for the frequency range of the collateral standard for EMC; and, (p) the average number of insurable claims of: manufacturer, handler, user, operator, medical care personal, medical facility, medical facility management or any combination thereof when utilizing the PNTI is v times lower than patient MRI associated insurable claims; v is equal or greater than 1.05 .

Reference is now made to FIG. 1A, schematically illustrating in an out of scale manner a cylindered embodiment of the invention. A perspective view of a neonate (1), situated within a passive thermo-regulated neonatal transport incubator (800), PNTI, having perforation through which the incubator is thermo regulated by any means in its external environment, and especially by any imaging device, medical imaging device, treatment device. The perforations can be evenly distributed throughout the incubator or in at least a portion thereof. The incubator (800) is configured by means of size and shape to accommodate a neonate (1) or any patient, or any body part thereof. Additionally or alternatively life support equipment and monitoring systems are incorporated with the incubator thereby providing a life supporting environment for the neonate. Further, the incubator can comprise a port configured for the passage of life supporting equipment or the docking thereof. Additionally or alternatively the neonate can reside freely within the incubator or restraint by restraining means such as belts, straps, hugger, concave shape and etc. Additionally or alternatively, the neonate is placed on a patient mattress or bed. The location and the height of the patient placement is as close as possible to the original patient bed within the imaging device, so the location of the patient is optimally placed in reference to the image device configuration (e.g. the magnetic fields of an MRI). The PNTI is permeable to such as any radiation, magnetic field, thermal imaging, and etc. Additionally or alternatively, the PNTI is permeable in a unidirectional manner or bidirectional manner, or any combination thereof. Additionally or alternatively, the PNTI is made of MRI safe materials. Additionally or alternatively at least part of the PNTI is configured to be inserted into an MRD bore. Additionally or alternatively, the PNTI is as depicted in U.S. Pat. No. 20130109956 A1, filed Jul. 7, 2011, titled "PREMATURE NEONATE LIFE SUPPORT ENVIRONMENTAL CHAMBER FOR USE IN MRI/NMR DEVICES" incorporated herein as a reference in its entirety.

Reference is still made to FIG. 1A, schematically illustrating a perspective view of a passively ventilated and/or thermo-regulated dependent transport neonate incubator (PNTI). It is in the scope of the invention wherein the PNTI (800) is useful for immobilizing or more freely accommodating premature babies, infants and toddlers, grown patients and laboratory animal in a thermo-regulated and/or a ventilated environment provided by an independently thermo-regulating and/or ventilating medical devices, such as incubators, carts, MRI devices and so on and so forth. The PNTI is made of perforated envelope. The envelope may be fully perforated or partially perforated. For example, the top part can be perforated to enable air circulation while the lower part may be imperforated to enable its placement on a surface with no risk of contamination of the inner part of the container. In one embodiment of the invention, the PNTI may be disposable and made for a single use. For example, the container may be a passive disposable container for transporting a neonate around the hospital. In an embodiment the PNTI can be at least partly made of a sterilizable material, or a completely sterilizable container. The PNTI may also be foldable for storage needs. It may be made of foldable material or comprise hinges enabling its folding. The PNTI comprises at least a portion of transparent material enabling at least partial imaging of a patient. In an embodiment the PNTI comprises sound attenuating means such as resonators, sound absorptive lining, sound isolating materials, active sound cancellation devices, and etc., configured to at least partially attenuate the sound of the environment external to the PNTI (e.g. the sound generated by an MRD).

Figure 1B:
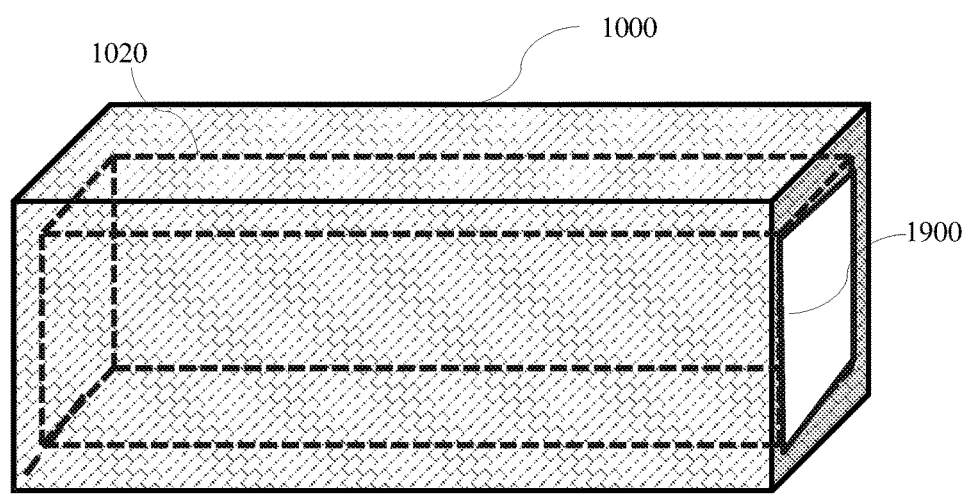
FIG. 1B, illustrating in an out of scale manner a passive neonates transport incubator (PNTI) in a rectangular embodiment.

Reference is now made to FIG. 1B, schematically illustrating in an out of scale manner a rectangular embodiment of the invention. A perspective view of a passive thermo-regulated neonatal transport incubator (1000), PNTI, having perforation through which the incubator is thermo regulated by any mean in its external environment, and especially by any imaging device, medical imaging device, treatment device, and etc. The PNTI is configured to accommodate a neonate/patient within in the incubator internal space (1020). The PNTI comprises at least one reversibly closeable opening (1900) configured so that the neonate, a handler's hand, a treatment device, or any combination thereof can enter the PNTI. This opening could be on any portion and any face of the incubator. Still referring to FIG. 1B and according to one embodiment of the invention, the PNTI (1000) is at least partially perforated provided with unidirectional or bidirectional breathing envelope. According to yet another embodiment of the invention, the container (1000) is at least partially transparent. According to yet another embodiment of the invention, the PNTI (1000) is collapsible, foldable or retractable. According to yet another embodiment of the invention the PNTI (1000) is a disposable envelope. According to yet another embodiment of the invention, the PNTI (1000) is at least partially made of MRI-safe materials, such as glass, composite materials, poly (trimethylene terephthalate) (PTT or likewise PET); poly (methylmethacrylate), (PMMA or likewise PHMMA); polyvinyl chloride (container) or blends based on these plastics.

Figure 2A:
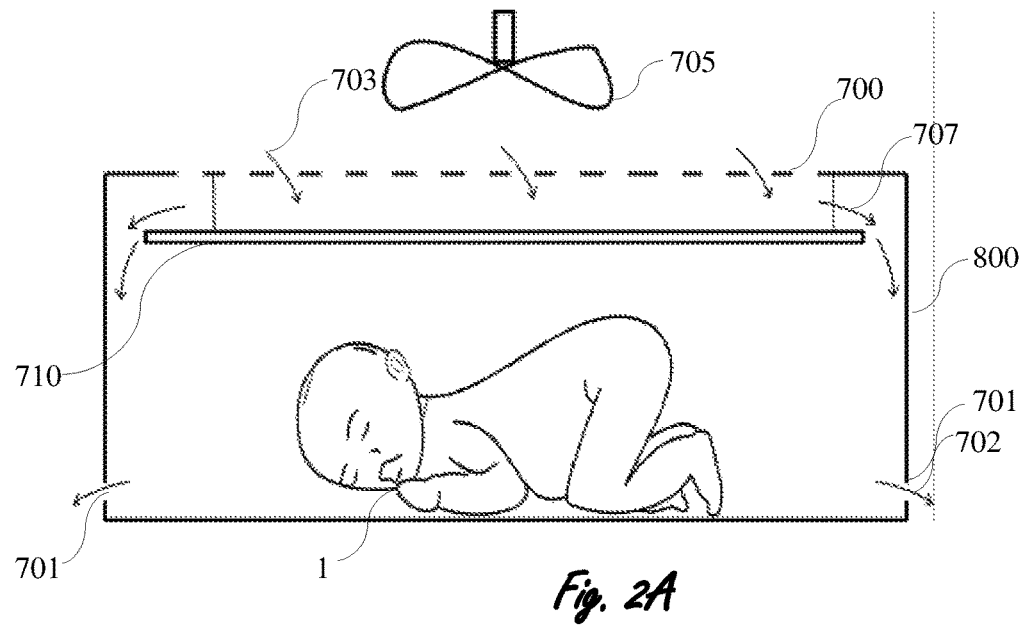
FIG. 2A, illustrating in an out of scale manner an embodiment of a PNTI in a section side view, having the air flow around a baffle.

Reference is now made to FIG. 2A, schematically illustrating in an out of scale manner a section side view of an embodiment of the invention. A PNTI (800) having perforations on top (700) and on the sides (701) through at least some of the perforations the PNTI is passively thermo regulated. The PNTI is located where an external ventilation system is employed (705), as a non-limiting example, in an imaging device. The Air flow within the incubator is configured to be not directly on the neonate by means such as a partial block (710) allowing the air to flow from the external space though the perforation (arrow 703) in the perimeter of the neonate shown by the arrow (707). In this embodiment the air flows out through the side perforations (701) and so the air within the incubator is recycled. In this embodiment no direct air flow is directed at the neonate and as such can help prevent contamination.

Figure 2B:
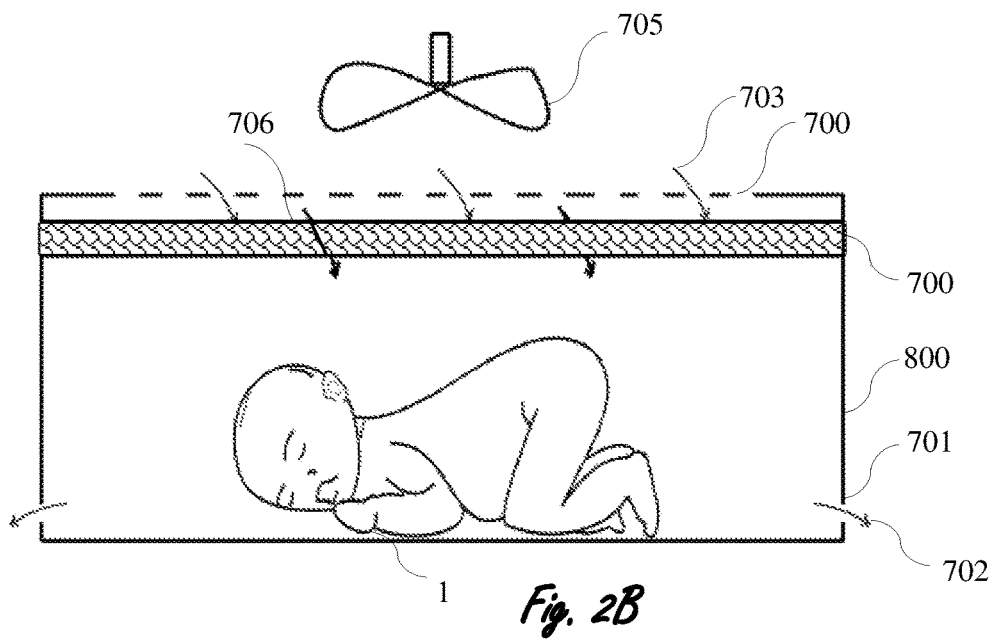
FIG. 2B, illustrating in an out of scale manner an embodiment of a PNTI in a section side view, the air flow is passing through a filter.

Reference is now made to FIG. 2B schematically illustrating in an out of scale manner a section side view of an embodiment of the invention. A PNTI (800) having perforations on top (700) and on the sides (701) through at least some of the perforations the PNTI is passively thermo regulated. The PNTI is located where an external ventilation system is employed (705), as a non-limiting example in an imaging device. The air flow into the incubator is configured to pass through an air filter configured filter any air borne particles such as smoke, microorganisms, liquid droplets, dust, aromatic molecules contaminants, and etc. The air flow from the external space though the perforation (arrow 703) to the vicinity of the neonate shown by the arrow (706). In this embodiment the air flows out through the side perforations (701) and so the air within the incubator is recycled.

Figure 3:
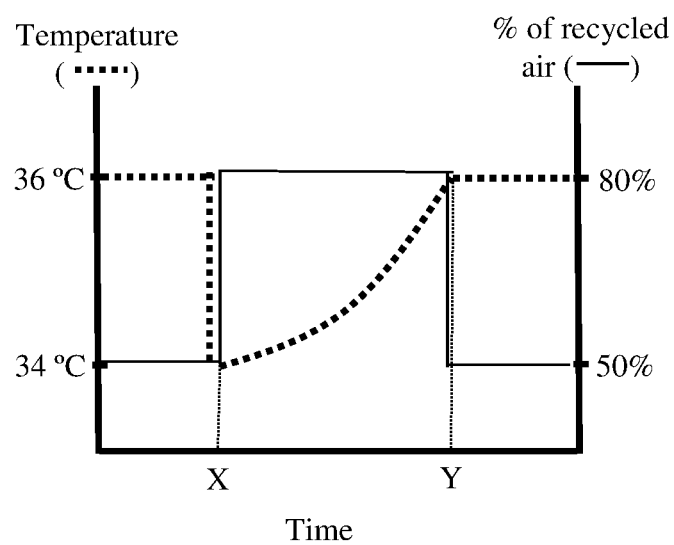
FIG. 3, illustrating in an out of scale manner the percent change of recycled air flowing to the PNTI at different temperatures.

Reference is now made to FIG. 3, schematically illustrating in an out of scale manner a graph demonstrating the change in the amount of recycled air flown into the PNTI according to the change of temperature. When the PNTI perforations are closed (either by a non-perforated outer layer, or any mechanism configured to open or close at least one perforation, such as hatch, shutter, screen, flexible material, shape changing polymer according to temperature as commercially available from CRG, Orlando, Fla. USA. Temperature is kept steady at 36° C. (before time point X), when the incubator is placed in a steady temperature environment. The amount of recycled air is also kept steady (50% in this example) by an external air streaming regulator. Once the PNTI is placed in an imaging device accommodated by a neonate (time point X), the temperature begins to fluctuate, and for example, the temperature inside the PNTI decreases and there is a need to re-heat it as quickly as possible. In response to the temperature change, within the PNTI the perforations are at least partly opened to increase the amount of recycled air flow from 50% to 80%. Since the recycled air is for example warm, it helps to return the temperature inside the PNTI back to 36° C. Once the temperature stabilizes the perforations are at least partly closed again. This activity can be according to local sensors configured to sense the air parameters of the internal and/or external air of the incubator, like as a non-limiting example temperature, humidity, drift, and gas concentration (e.g. $O_2$, $CO_2$, and etc.) The sensors can further transmit the sensed information to a CPU, a control device, a monitoring device, a mobile network, a local wireless network, the Internet and etc. The perforations can be opened by a small engine connected to a maneuvering device of a window or shutter, or mechanism responsive to stimuli such as light, electricity, temperature, exposure to liquid and etc. The opening and or closing can be done manually, automatically or both. The opening and/or closing can be configured to respond to a predetermined cue, or predetermined sensed information, trigger an alarm, predetermined neonate condition, manual operation, and etc.

Figure 4A:
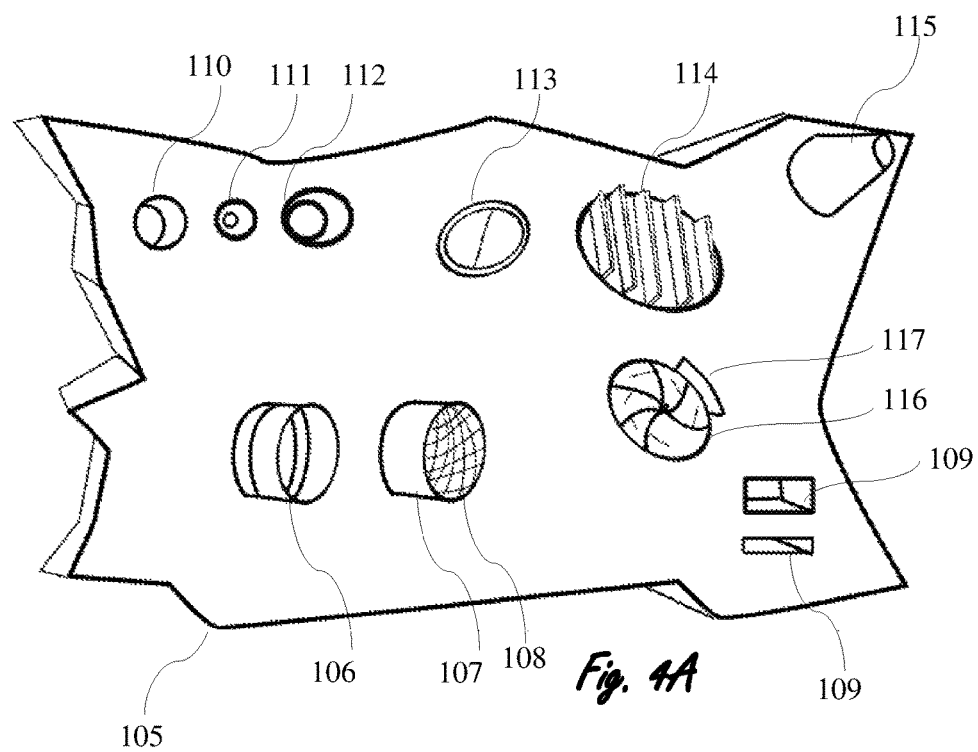
FIG. 4A, illustrating in an out of scale manner a portion of a PNTI showing examples of different perforations and/or openings for the PNTI.

Reference is now made to FIG. 4A schematically illustrating in an out of scale manner embodiments of the invention. Shown is a portion of an incubators face (105), comprising various embodiments of perforations (106-117). The perforations can be similar, variable or a combination of both. The perforations can be permanently opened (106, 110, 111, 112, 109, 115), or at least partly closeable (113, 114, 116, 107). The permanently opened perforations can be closed by an external seal. The perforations can have walls protruding from the incubators face (115, 106, 107) or not (110, 112, 111, 113, 114, 116, 109). The perforations are of any shape such as round (110), rectangular (109), polygonal, symmetrical or non-symmetrical. The perforation can be in an angle to the incubators face (106, 107, and 115) or parallel to it (113, 109, and 110). The perforation can comprise a narrowing opening (111) an opening closable by a baffle, or a maneuverable shutter (114), a restrictor (116), or a filter (108). Additionally or alternatively the perforators can comprise a signal receiving domain (117) receiving a signal to open and/or close the restrictor. The signal can be received by wire or wirelessly, by such as RF, blue tooth, infrared, sound, light, or any other transmission mean. Additionally or alternatively, the perforations comprise a flexible material made from a memory shape polymer configured to be change between an opened or closed configuration according to stimulus.

Figure 4B:
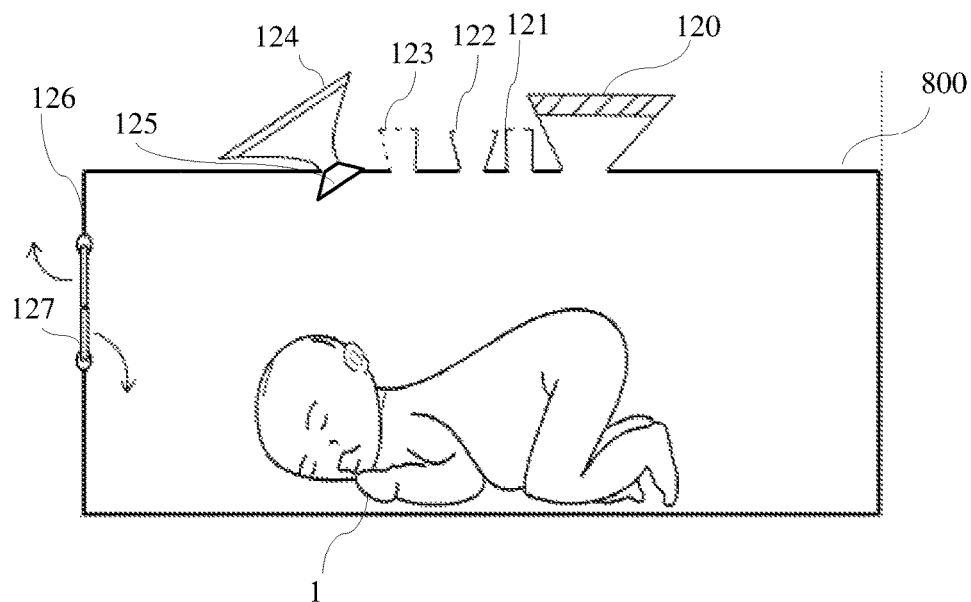
FIG. 4B, illustrating in an out of scale manner an embodiment of the invention in a side section view, showing various embodiments of perforations and/or openings of the PNTI.

Reference is now made to FIG. 4B schematically illustrating a section side view of an embodiment of the invention. Illustrated is a PNTI (800) in a rectangular embodiment, accommodating a neonate (1) comprising various embodiments of protruding perforations (120-123). At least one of the perforations (120) can comprise an air filter. The protrusions can comprise a single opening (121, 122) or multiple (123). Additionally or alternatively, the perforations can be configured to be opened and/or closed (122). Additionally or alternatively, the perforation can be connected to a removable device (124) comprising such as an air filter, a baffle, an angled shutter directing the air flow (125), a humidifier, an air circulating device, and etc. Additionally or alternatively, the PNTI comprises at least one opening. This opening is such as: a door, a sleeve, configured for the passage of a handlers hand, or any treatment device, and etc. The opening is as a non-limiting example comprised of a maneuverable hinge (126) connected to a moveable panel (127), and can be configured to open outward, inward, or any combination thereof.

Figure 5A:
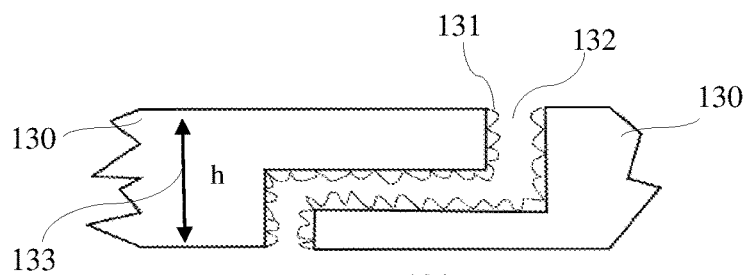
FIG. 5A-G, illustrating in an out of scale manner a section cut of the PNTI wall comprising different embodiments of perforations.
Figure 5B:
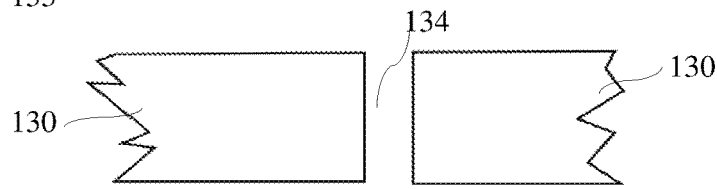
Figure 5C:
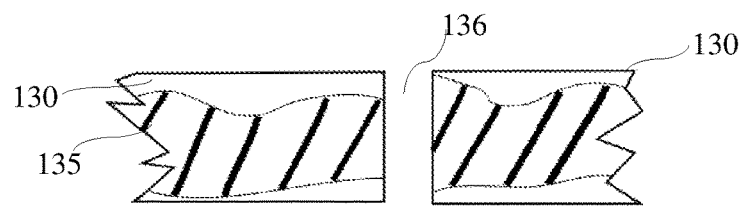
Figure 5D:
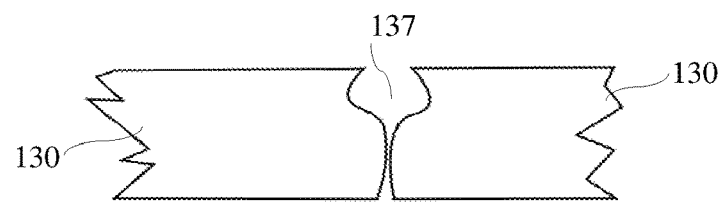
Figure 5E:
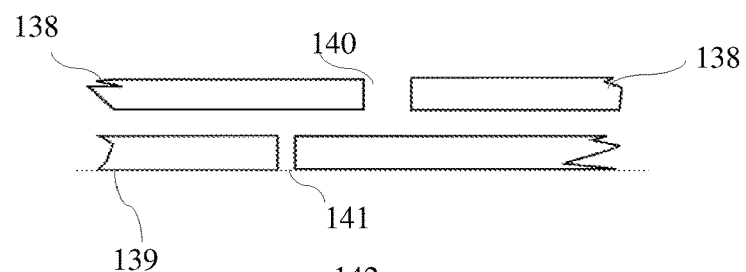
Figure 5F:
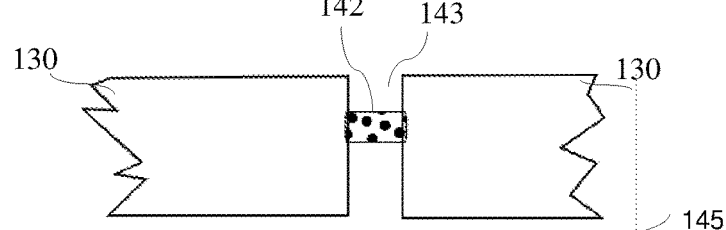
Figure 5G:
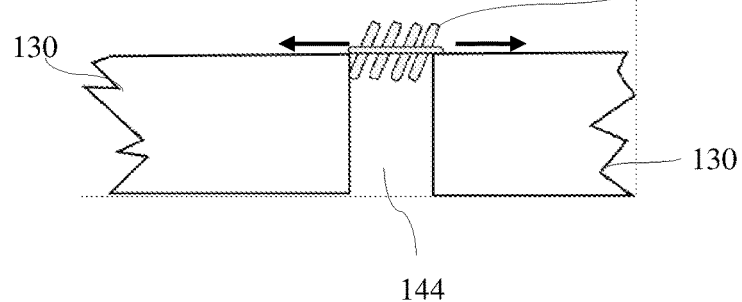

Reference is now made to FIG. 5A-G schematically illustrating different embodiments of a section side view of the PNTI's perforations. FIG. 5A illustrates h as the thickness (133) of the wall (130) of the PNTI. The value of h is variable, constant or any combination thereof. The air is passed into and/or out of the incubator through an indirect passage (132), additionally or alternatively lined with at least partially sound absorptive material (131). FIG. 5B illustrates a direct passage (134) for the air within the wall (130) of the PNTI. FIG. 5C illustrates a direct passage of air (136) through the PNTI wall (130). The PNTI wall (130) further comprises a filler material configured to at least partially isolate the inner volume of the incubator from the external environment like for example sound, temperature, and etc. FIG. 5D illustrates a non-symmetrical perforation (137) along the depth of the PNTI wall (130). This perforation can be configured to function as a resonator configured to cancel out a predetermined sound frequency. FIG. 5E illustrates an embodiment of the invention showing the wall of the PNTI comprised of two walls (138, 139) having an air space between them. Each wall can comprise a perforation (140, 141) that can be in a direct line fluid connection with the latter or in an indirect line of fluid connection with the latter. Additionally or alternatively the distance between 138, and 139 can be constant, variable or a combination thereof along different portions of the PNTI. FIG. 5F illustrates in an out of scale manner a section of an embodiment of incubator wall (130) comprising at least one perforation (143). The perforation is at least partly masked by an air filter (142). FIG. 5G schematically illustrates another embodiment of a PNTI wall (130) having a perforation (144) in a section side view, connected to a maneuverable shutter (145), moveable in the direction of the arrows, configured for directing the air flow in different directions.

Figure 6A:
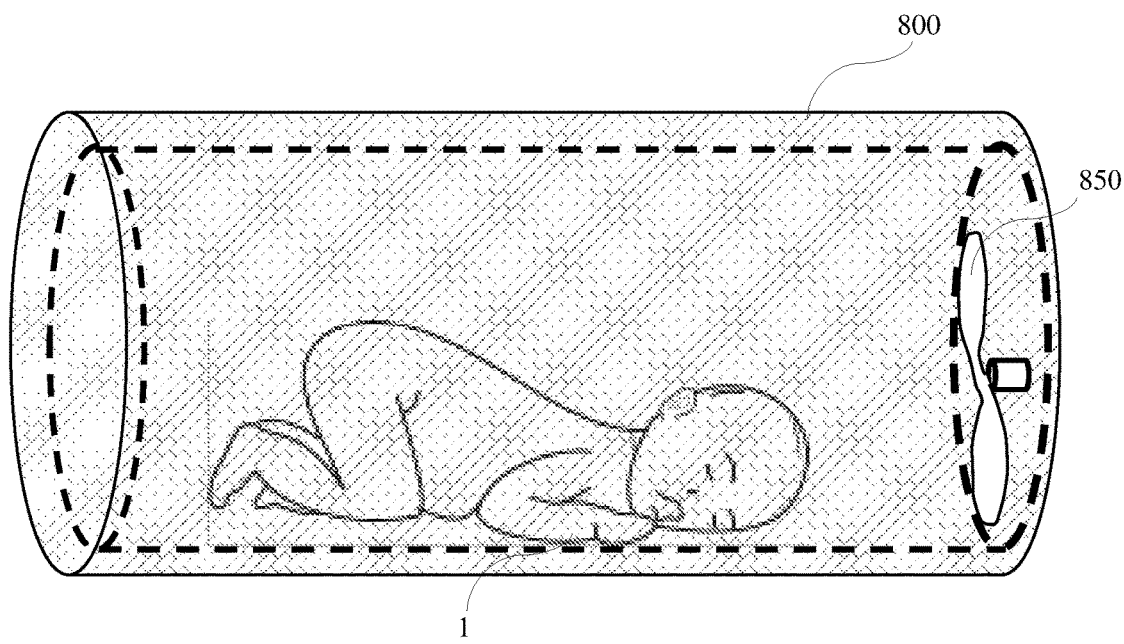
FIG. 6A, illustrating in an out of scale manner an embodiment of a PNTI comprising a venting module.

Reference is now made to FIG. 6A schematically illustrating in an out of scale manner an embodiment of the invention. A perspective view of a comprising an envelope at least in portion perforated comprising a venting mechanism, such as a fan or a Dyson bladeless air multiplier. It is in the scope of the invention wherein the PNTI (800) is useful for immobilizing or more freely accommodating premature babies (1), infants and toddlers, grown patients and laboratory animal in a thermo-regulated environment provided by independently thermo-regulating medical devices, such as incubators, carts, MRI devices and so on and so forth.

The PNTI may be thermo-regulated or ventilated by a thermo-regulating and/or venting medical device. For example, a cart used for transporting the container may also thermo-regulate the PNTI while it is in transit. The PNTI can also be thermo-regulated by a thermo-regulating MRI while the neonate is being imaged. In a similar manner, the PNTI can be thermo-regulated by a CT scanner, an X-ray device or any other medical device.

According to yet another embodiment of the invention, the envelope (800) comprising or otherwise is in connection, preferably in fluid connection, with one or more of the following: venting means, such as a second fan; heating/cooling means, such as a Pelletier module or thermo-regulating blanked or air conditioning arrangement; humidifying means, audio/video means, life support system or interface thereof; light emitters, at least one sensor, a CPU, at least one indicator, at least one regulator and/or controller, and any combination thereof. Additionally or alternatively, the capsule is also connected to a thermo regulated vent for thermo-regulating it above on only ventilating it.

Figure 6B:
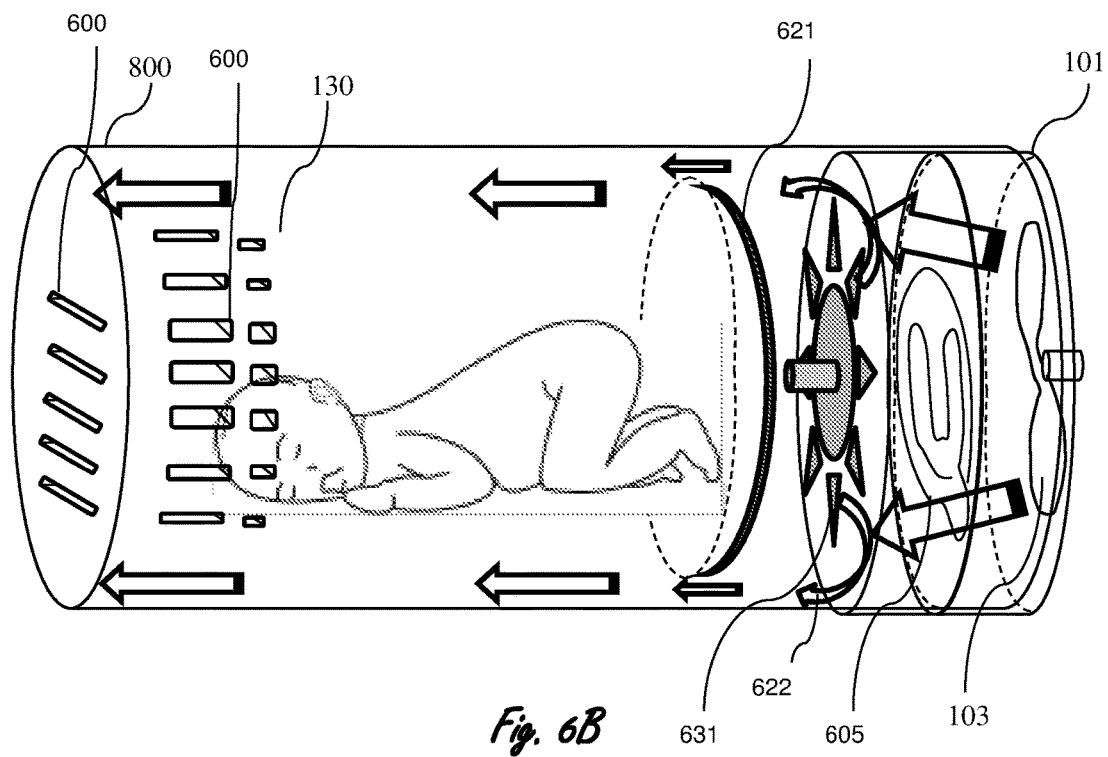
FIG. 6B, illustrating in an out of scale manner an embodiment of the PNTI comprising perforations on at least a portion of the PNTI, further comprising a venting module, with a heating device, turbulating device, and a baffle.

Reference is now made to FIG. 6B schematically illustrating in an out of scale manner an embodiment of the invention. A partially perspective side view of a PNTI (800), comprising an envelope configured to accommodate a neonate (1), comprising perforations (600) according to yet another embodiment of the invention. The PNTI (800) comprises a variant of the aforesaid fluid venting module. Here, the venting system comprises at the PNTI's proximal end (101) at least one Thermoregulation system comprising a venting module (e.g., fan 103), heating/cooling module (605) and a wind baffler (621). In at least one predefined location, e.g., between the heating/cooling module and the baffler, there an air turbulating means is further located (631). This can be a pre-fan or post-fan ventilator adapted to a relatively slow rotation to gentle air stream (622) before or after its baffling. The turbulating means are selected in a non-limiting manner from active members, such as fan, multiple-fan arrangement or cascade thereof, air pump, Dyson-type bladeless air multiplier, venting apparatus etc., and/or passive members, such as texturized strainer, curved conduits in a continuous barrier etc. The air baffler can be a plurality of bafflers, situated in any location between the neonate and the origin of the air flow in the proximal end, in the distal end or anywhere in between. The airflow (622) facilitated by fan 103 is heated (605) and streamed towards baffler (621), which is, e.g., a curved member, polygonal member, a texturized surface, a shaped surface comprising one or more apertures etc. In an embodiment the air flows through an air turbulating mean. The air flow is configured to be parallel to the neonate (1) body positioned head wise or leg wise to the air flow.

Figure 7A:
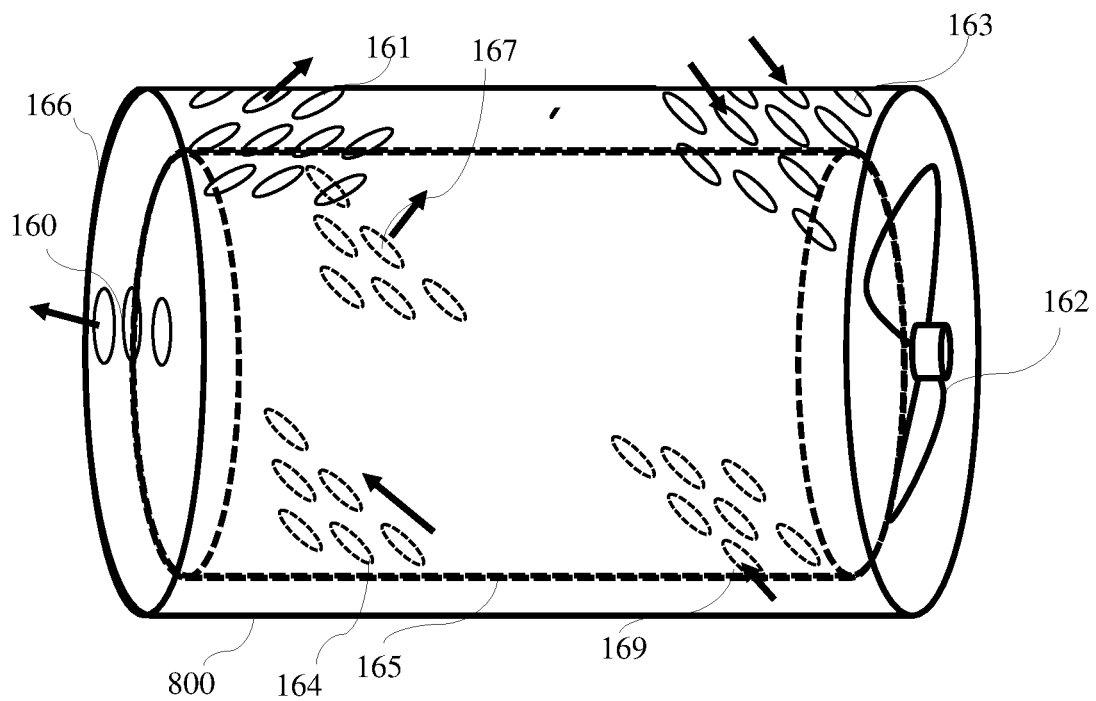
FIG. 7A, illustrating in an out of scale manner an embodiment of the invention, a PNTI comprising two perforated envelopes and connected to a venting module.

Reference is now made to FIG. 7A, schematically illustrating in an out of scale manner an embodiment of the invention. A perspective drawing of a PNTI (800), in an embodiment comprising two partly perforated envelopes (165, 166), and a venting module, e.g., a fan, a jet, a blower, a compressor, a pump etc., (162), connected at least to the external envelope (166) configured to stream air from the external environment to the inner volume. The air is forced to pass between the two envelopes in a circular manner, having the air intake from perforations (163) either unidirectional or bidirectional and streamed around the inner envelope (165) entering the inner envelope through perforations (169, 164). The air exits as a non-limiting example through perforations (167) of the inner envelope (165), located adjacent to the air exit perforations (160, 161) of the outer envelope (166). The circulation of air provides a rapid mean of air recycling and a more efficient manner of temperature regulating the PNTI. In addition whether the venting module is operative or not, the PNTI (800) receives passive ventilation from its environment through any of its perforations.

Additionally or alternatively, the PNTI further comprises at least one first fluid heating/cooling module (e.g., an air conditioned system, an infrared heater, a water/oil-heated radiator, a coiled heater, an open coil air heater, a round open coil air heater, a convection heater, straight or formed tubular heaters, a quartz tube air heater, a capacitor-type heater, a Pelletier module or any combination of the same).

The inner envelope is configured by means of size and shape to accommodate a neonate, and the outer envelope is configured by means of size and shape to be reversibly housed within a medical apparatus such as an imaging device, a treatment table, an operating table, and etc.

Additionally or alternatively, the ratio between the amount of air flown into the PNTI from the two sources (externally passively supplied vented and/or thermo regulated air, and venting and/or thermo regulated air supplied by a venting module connected to the PNTI) is controlled by a regulator. When the PNTI is accommodated by a neonate and in a temperature steady environment, the regulator enables mostly air from the surroundings to flow into the PNTI. This air is rich in oxygen. However, when the PNTI is opened or the environment temperature changes, the regulator enables flow from a thermo regulated venting module streaming recycled air into the PNTI that although has low concentrations of oxygen, and helps maintaining a desired temperature. The regulator may enable the flow of mixed air in different ratios according to the degree of the drop in the temperature and the oxygen concentration inside the PNTI.

Figure 7B:
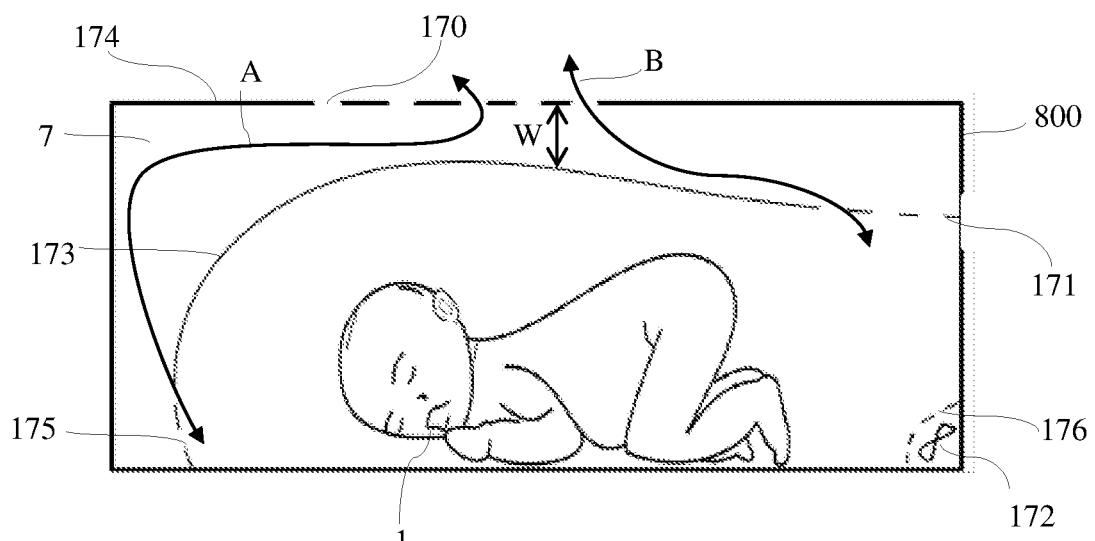
FIG. 7B, illustrating in an out of scale manner an embodiment of the invention, a PNTI comprising two envelopes with a variable distance between them.

Reference is now made to FIG. 7B schematically illustrating an embodiment of the invention, showing a side section view of an embodiment of the PNTI. The PNTI (800) comprises an external envelope (174) and an internal at least partial envelope (173) thereby forming an air conduit (7)

between the external environment and a neonate (1) residing within the internal envelope (175). The width of air conduit between the two envelope walls (w), is constant or variable. The air conduit is at least partially perforated, configured to stream air indirectly from the external environment towards the location of the neonate, as indicated by arrows A, and B. In an embodiment the PNTI comprises air turbulating means (172) configured to speed the air recycling within the inner envelope. In an embodiment, the turbulating means can be connected to a sensor, a CPU, a regulator, controller, and etc., which control and regulate the operation thereof according to parameters set by the user.

Figure 8:
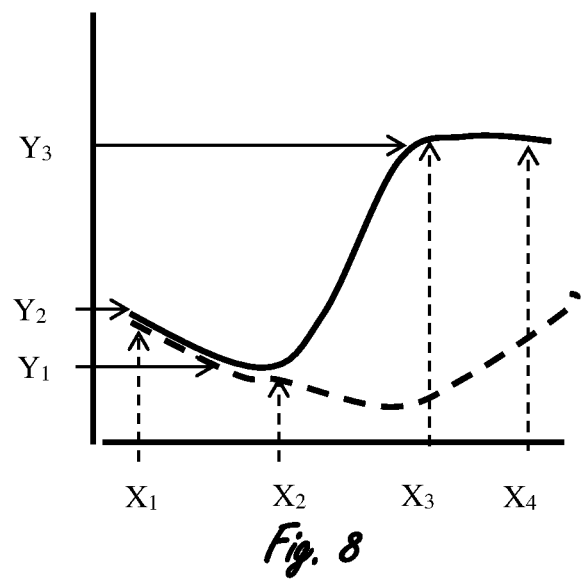
FIG. 8, illustrating in a non-in-scale manner the difference in time ($\Delta T$) for changing the temperature utilizing a linear flow and a turbulent flow.

Reference is now made to FIG. 8 illustrating in a non-in-scale manner the difference in time (ΔT) for changing the temperature utilizing a linear flow and a turbulent flow. Linear flow can be provided to the PNTI by an external thermo regulating venting module, while turbulent flow can be provided by further introducing a venting module into or in fluid connection with the PNTI. The graph in the figure describes the time it takes a PNTI to return to its designated temperature after an event causing a shift in that temperature. $X_1$ represent the time in which an event has occurred (like opening the door of the incubator) which causes a decrease in the temperature (from temperature $Y_2$ which is the designated temperature). Point $X_2$ presents the time in which the Thermo regulating venting module starts warming the PNTI. The continuous line represents warming by turbulent flow while the broken line represents warming by linear flow. It can be observed that turbulent flow warms the PNTI environment much faster than linear flow.

Figure 9:
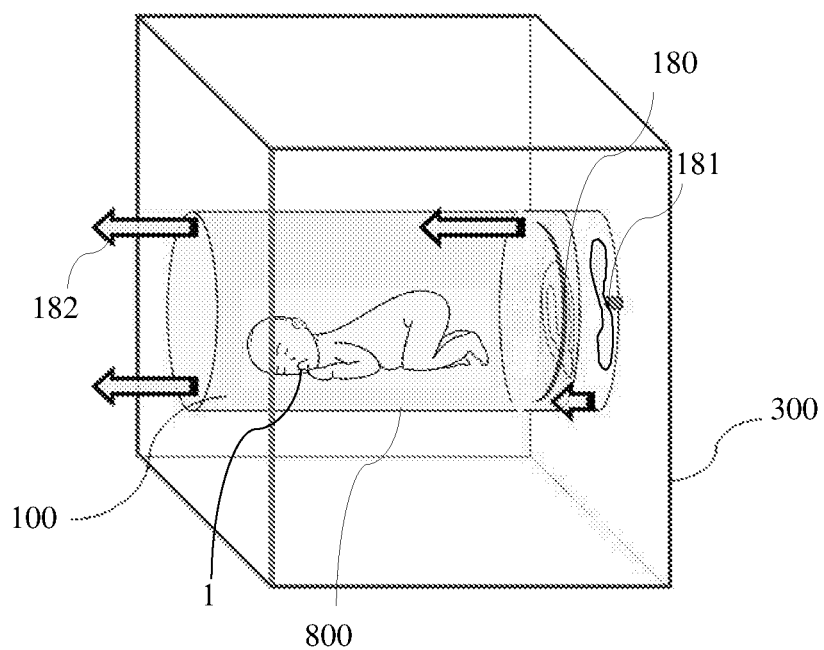
FIG. 9, illustrating in an out of scale manner an embodiment of the invention, a PNTI comprising a venting module inserted into an imaging device.

Reference is now made to FIG. 9, illustrating in an out of scale manner an embodiment of the invention. Shown is a perspective view of the PNTI, comprising an at least partly perforated envelope, accommodating a neonate (1), connected in its distal end a thermo regulating venting module. The venting module comprises at least one air streaming means (e.g. a fan, 181), and an air heating module (180) through which the air is passed towards the neonate, in a linear parallel flow (182) to the body of the neonate. Further, the PNTI is configure to be at least partially inserted into an MRD (300) bore (100) enabling scanning the neonate accommodated within. The thermo regulating venting module can be connected in any of the PNTI ends, and may protrude out of the MRD bore on either side.

Reference is now made to FIG. 10A, schematically illustrating an embodiment of the invention. A perspective view of the PNTI (800), comprising an at least partly perforated envelope (261) configured by means of size and shape to accommodate a neonate (1) within, surrounded by a second external solid envelope (260), unperforated. A thermo regulated vent (1001) is connected to one of the elongated shape's ends allowing the streaming of air from the external environment into a space formed between the envelopes. The air flows through a heating/cooling module (121A). Additionally or alternatively, the thermo regulated venting module comprises at least one air filter and at least one baffler (1022). The incubator comprises, within its inner portion, an arrangement of double-jacket walls formed for example, by an outer envelope comprising an upper double-wall arrangement (250) and an inner envelope (251). Those inner and outer walls which envelop the infant (1) are layered in a manner that provides an effective air flow (1008). The outer wall can be a continuous envelope or at least partially perforated envelope. Additionally or alternatively, the outer envelope comprises at least one air exit port and/or at least one air inlet. The inner wall is at least partially perforated. The air-conduit provided by walls of the two envelopes is characterized by a width (w). The value of w is equal along air conduit (253), namely along the longitudinal axis (1001-102), or not equal, to have at least one portion of a small width (w), and at least one portion of relatively large width (W), where W>w.

In one example of such a system, ambient air is streamed from e.g., the proximal end (101) to the e.g., distal end (102) by a fan and thermo-regulated by a heater. It is then continuously or non-continuously forced by a baffler (1022) to a conduit of width (w) provided within the upper (infant's ceiling side) double jacket of wall (260, 261). Inner wall (261) is perforated thereby air is allowed to circulate, evacuating air with respectively high carbon dioxide concentration from the inner environment of the incubator (254) and inflowing air with respectively low carbon dioxide concentration, whilst thermo-regulating the environment (254). Reference is still made FIG. 10A, illustrating a lower double jacket (infant's bedside) provided by two concentric parallel layers of non-perforated external wall (260) and perforated inner wall (261) providing liner air flow (1008) to an effective yet gentle air circulation (201).

According to yet another embodiment of the invention, the PNTI (800) has a round or a polygonal form, a single enveloping wall or a multiple enveloping walls. According to yet another embodiment of the invention, the PNTI (800) comprises at least one opening where an infant can be inserted from. In one embodiment of the invention, the PNTI inner envelope is disposable and made for a single use. For example, the container may be a passive disposable container for transporting a neonate around the hospital.

Reference is now made to FIG. 10B, schematically illustrating in an out of scale manner, a cross-section of a portion of the upper (neonate's ceiling side) double jacket of the walls (260, 261) in non-limiting manner. Here again, thermo-regulated air flow (1008) is streamed from the proximal side of the incubator (101). Width (w) is equal along the conduit (253) providing air inflow and outflow (202B, 202A).

Reference is now made to FIG. 10C, schematically illustrating in a non-limiting out of scale manner, a cross-section of a portion of the upper (infant's ceiling side) double jacket of the walls (260, 261). Thermo-regulated air flow (1008) is streamed from the proximal side of the incubator (101) via conduit (253). Width is varied in a manner that initial width (w) is narrow and then width increases (W). Due to a Venturi effect, high pressure, clean and thermo-regulated air stream at the proximal side of the conduit efflux (202A) towards the inner environment of the incubator (254). At the distal portion of the conduit, width (W) is respectively greater, and again, due to a Venturi effect, the air pressure decreases and air influx (202B) into the conduit via the perforated inner wall (251) is easier. Conduit 253 expands its width at location (1054). Thus, when neonate's mouth is facing location (1054), where conduit 253 expands its width, or otherwise located adjacent to the area, carbon dioxide is effectively, silently and safely evacuated from the area surrounding the infant mouth. At the same time, thermo-regulated clean air is forced in a controlled manner to the infant's surroundings at a location located remotely to neonate's head.

Reference is now made to FIG. 10D, schematically illustrating in a non-limiting, out of scale manner, a cross-section of a portion of the upper neonate's ceiling side the double jacket formed from walls (260, 261). Here again, thermo-regulated air flow (1008) is streamed from the proximal side of the PNTI (101) via the conduit (253). Width is varied in a manner that initial width (W) decrease along the conduit to a width (w) due to a Venturi effect which was described above, low pressure stream of air in the proximal side of the conduit evacuate carbon dioxide rich air flow towards the conduit (253), whilst high pressure air stream at the distal side forces clean and thermo-regulated air flow from the conduit towards the inner environment of the PNTI (254). Additionally or alternatively, this configuration causes turbulent air flow, unlike laminar air flow in FIG. 10B, that facilitates a faster temperature change of the space formed between the two walls.

Reference made to FIGS. 10B-D. Similar to FIGS. 10C and 10D showing changes in the width (w) along the conduit, changes can also occur in the length (l) of the conduit and cause similar Venturi effect.

Figure 11:
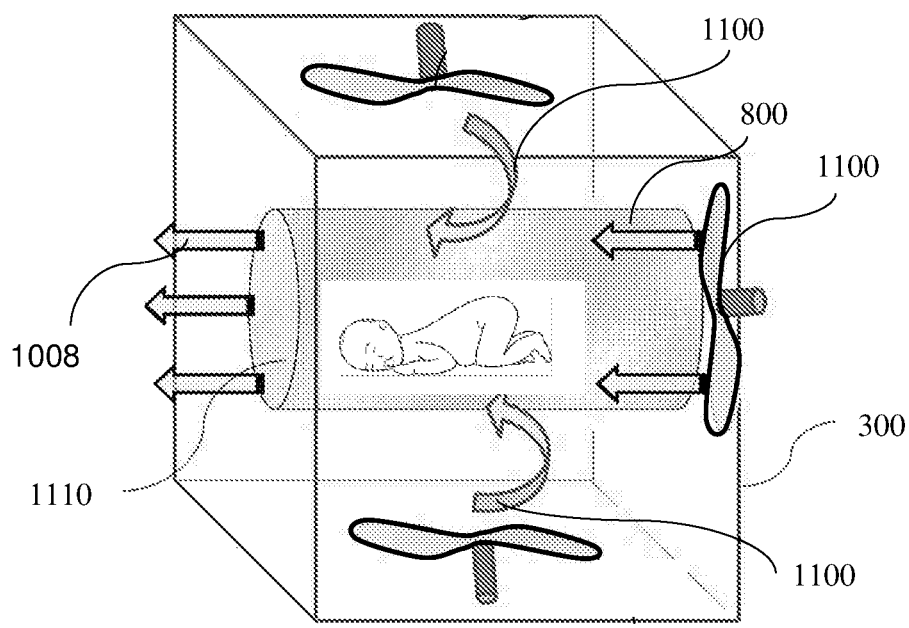
FIG. 11, schematically illustrating an embodiment of the invention, a PNTI inserted within an independently ventilated medical device (e.g. MRI)

Reference is now made to FIG. 11, illustrating in a non-limiting, out of scale manner, an embodiment of the invention. A PNTI (800), comprising an elongated envelope, configured by means of size and shape to accommodate a neonate, baby, toddler, patient, animal and etc. The envelope has outer dimensions configured to be accommodated within a medical analyzing device, a medical scanning device, a medical imager (e.g. MRD, x ray, CT scanner, cart. incubator), a medical treatment device or apparatus, an operating table/apparatus and etc. (300), having means for venting the air within the device, at least in the location of the designated patient table, such as a venting module, a heating/cooling air streaming device, a thermo regulated vent, a humidifier, a specific concentration of predetermined gas suppliers, and etc. The air flow (1008) streamed from the medical device enters the PNTI through perforation and/or at least one opening and streamed through perforations on at least one end. The air flow from the medical device is streamed from any direction (1100) above, beneath, behind (e.g. from a distal side of an MRD open bore) and any combination thereof. The perforations in the proximal end of the PNTI, situated, for example, near the opening of an MRD open bore (1110) function mainly as air outlet ports when the PNTI is in the ventilated device. There is no equipment based above or below the ANTI, which makes it highly suitable for imaging, especially in an MRI where the location of the scanned subject is critical for good quality imaging in reference to the magnetic field iso-center. The PNTI provides a solution for thermo-regulating neonates during various examinations medically issued, for example being thermo regulated while imaging.

In one embodiment of the invention, the PNTI may be disposable and made for a single use. For example, the container may be a passive disposable container for transporting a neonate around the hospital.

The PNTI may also be foldable for storage needs. It may be made of foldable material or comprise hinges enabling its folding.

Still referring to FIG. 11, schematically illustrating a perspective view of a PNTI for ventilated and/or thermo-regulated by a ventilating and/or thermo-regulating MRI device (300). The PNTI, (800) having all means for standing all applied regulations, especially the following standards and sections thereof: ANSI/AAMI/IEC 60601-2-20:2009 Medical Electrical Equipment—Part 2-20: Particular requirements for the basic safety and essential performance of infant transport incubators; and more specifically to section 201.3.201; AIR CONTROLLED TRANSPORT INCUBATOR in which the air temperature is automatically controlled by an air temperature sensor close to a value set by the OPERATOR; 201.3.202 AVERAGE TEMPERATURE average of temperature readings taken at regular intervals at any specified point in the COMPARTMENT achieved during STEADY TEMPERATURE CONDITION; 201.3.203 AVERAGE TRANSPORT INCUBATOR TEMPERATURE average of the INFANT TRANSPORT INCUBATOR TEMPERATURE readings taken at regular intervals achieved during STEADY TEMPERATURE CONDITION; 201.3.204 BABY CONTROLLED TRANSPORT INCUBATOR AIR CONTROLLED TRANSPORT INCUBATOR which has the additional capability of automatically controlling the INCUBATOR air temperature in order to maintain the temperature as measured by a SKIN TEMPERATURE SENSOR according to the CONTROL TEMPERATURE set by the OPERATOR NOTE An INFANT TRANSPORT INCUBATOR operating as a BABY CONTROLLED INCUBATOR is a PHYSIOLOGIC CLOSED-LOOP CONTROLLER as defined in IEC 60601-1-10.; 201.3.205 COMPARTMENT environmentally-controlled enclosure intended to contain an INFANT and with transparent section(s) which allows for viewing of the INFANT; 201.3.206 CONTROL TEMPERATURE, temperature selected at the temperature control; 201.3.207 INFANT PATIENT up to the age of three months and a weight less than 10 kg; 201.3.208 INFANT TRANSPORT INCUBATOR, TRANSPORTABLE ME EQUIPMENT that is equipped with a COMPARTMENT and a TRANSPORTABLE electrical power source with the means to control the environment of the INFANT primarily by heated air within the COMPARTMENT; 201.3.209 SKIN TEMPERATURE, temperature of the skin of the INFANT at a point on which the SKIN TEMPERATURE SENSOR is placed; 201.3.210 SKIN TEMPERATURE SENSOR sensing device intended to measure the INFANT'S SKIN TEMPERATURE, all incorporated herein in its entirely as a reference.

Figure 12:
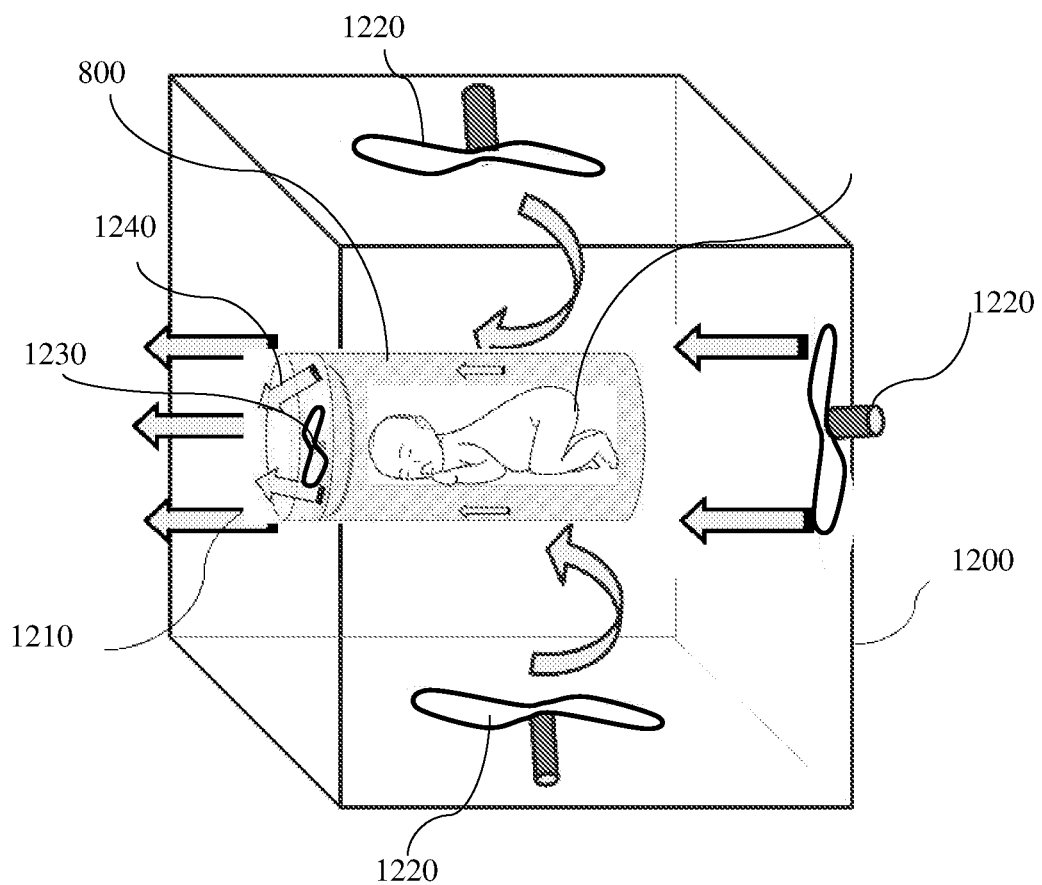
FIG. 12, schematically illustrating an embodiment of the invention, a PNTI additionally comprising a venting module inserted within a medical device.

Reference is now made to FIG. 12, schematically illustrating in a non-limiting, out of scale manner, a perspective view of a PNTI (800) ventilated and/or thermo-regulated by a ventilating and/or thermo-regulating MRI device (1200). The PNTI (800) and regulating MRI device having all means for standing all applied regulations, especially the aforesaid standards and sections thereof. FIG. 12 presents means and methods according to an embodiment of the invention for imaging a premature infant in an independently thermo-regulated gear, including independently thermo-regulated MRI (IT-MRI), and an independently thermo-regulated neonate's incubator (ITNI). The medical independently ventilated device (1200) comprising at least one venting modules (1220), that could stream air in the direction of the PNTI located within the device from any direction such as above, beneath, the back, and any combination thereof while the air circulates out from the front (as a non-limiting example, the proximal side opening of an MRD bore). The air passes through the PNTI perforations. The PNTI can also be connected to a venting module that can be reversible attached or detached form the PNTI (1230) further configured to stream the air (1240) out of the PNTI (800) and/or into the PNTI when in need.

In an embodiment, the medical device is configured to also stream air from the front of the PNTI, having the air steamed in the opposite direction to exit in a specially constructed port in the medical devices distal side.

Figure 13A:
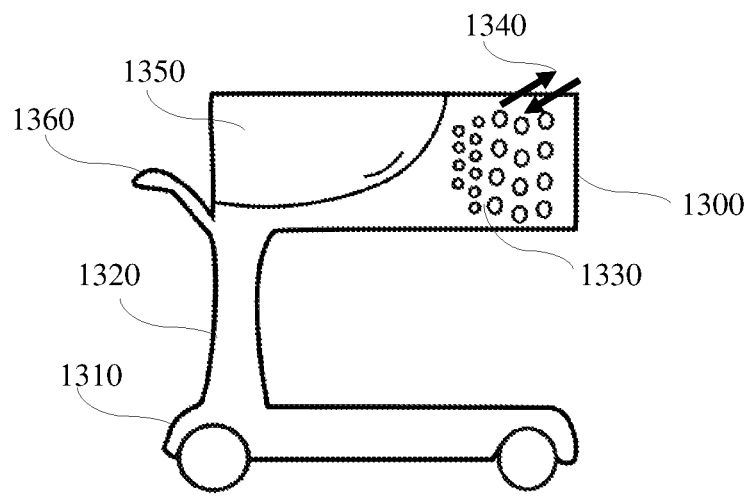
FIG. 13A, illustrating in an out of scale manner a side view of a PNTI on a cart.

Reference is now made to FIG. 13A illustrating in an out of scale manner an embodiment of the invention. A side view of a PNTI (1300) in connection with a cart (1360). In an embodiment the cart is made of MRI safe materials. The cart comprises a mobile base (1310), and at least one support column (1320). The PNTI comprises perforations (1330) unidirectional, bidirectional (1340) or any combination thereof. The perforations enable the PNTI to be passively thermo regulated by the environment is positioned in, or by an independently thermo regulation medical device (e. g. MRD comprising a bore ventilating module). The PNTI is permeable to such as: any radiation, magnetic field, RF, X-ray, thermal imaging, and etc. The PNTI comprises at least a portion of transparent material (1350) enabling at least partial imaging of a patient. In an embodiment the cart is insertable into an MRI bore as depicted in U.S. patent application 61/994,901, titled: "AN MRD ASSEMBLY OF SCANNER AND CART", filed on 18 May 2014.

Figure 13B:
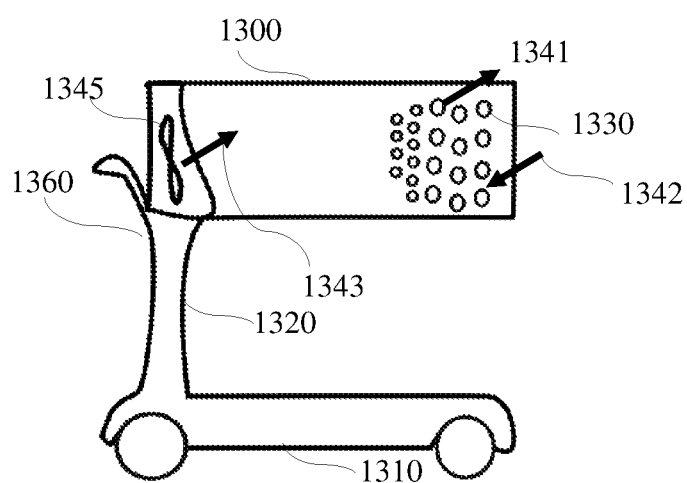
FIG. 13B, illustrating in an out of scale manner a side view of an embodiment of a PNTI in connection with a cart, connected to at least one venting module.

Reference is now made to FIG. 13B, illustrating in an out of scale manner an embodiment of the invention. A side view of a PNTI (1300) in connection with a cart (1360). In an embodiment the cart is made of MRI safe materials. The cart comprises a mobile base (1310), and at least one support column (1320). The PNTI comprises perforations (1330) unidirectional (1341, 1342), bidirectional or any combination thereof. The perforations enable the PNTI to be passively thermo regulated by the environment is positioned in, or by an independently thermo regulation medical device (e. g. MRD comprising a bore ventilating module). The cart in connection with the PNTI comprise at least one venting module connected continuously to the PNTI end (the proximal or distal, or both. The venting module (1345) comprises at least one air streaming device (such as a fan, compressor, a blower and etc.) configured to stream air into the PNTI (1343), out of the PNTI or both. Additionally or alternatively, the venting module comprises a heating and or cooling device, at least one air filter, a regulator, a controller, a humidifier, at least one baffle, and any combination thereof. The cart and/or cart can, in an embodiment, further comprise life support equipment or ports and/or connections for life support equipment. The cart The PNTI is permeable to such as: any radiation, magnetic field, RF, X-ray, thermal imaging, and etc. The PNTI comprises at least a portion of transparent material enabling at least partial imaging of a patient. In an embodiment the PNTI comprises sound attenuating means such as resonators, sound absorptive lining, sound isolating materials, active sound cancellation devices, and etc., configured to at least partially attenuate the sound of the environment external to the PNTI (e.g. the sound generated by an MRD). Additionally or alternatively, the PNTI can be reversibly installed onto a cart (1360).

Figure 13C:
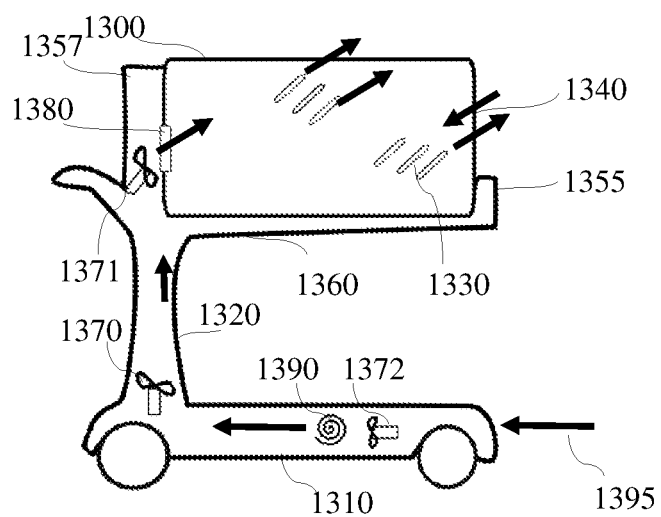
FIG. 13C illustrating in an out of scale manner a side view of an embodiment of the invention, a PNTI reversibly connected to a cart, the cart comprising a venting module.

Reference is now made to FIG. 13C illustrating in an out of scale manner an embodiment of the invention. The PNTI is reversibly installed on a cart (1360) having a mobile base (1310), and an upper shelf (1355) connected by at least one support (1320). The PNTI is configured for accommodating a neonate/patient within. In an embodiment, the PNTI can be disposable, and changed before every use, or for each neonate or patient. The PNTI can be permanently installed or temporarily installed. The PNTI comprises perforations (1330) that are unidirectional, bidirectional or both (1340). These perforations allow the PNTI to be passively vented and/or thermo regulated by a system or module external to the PNTI. The cart comprises at least one venting module located in the cart base (1310), in the cart support (1320), in the cart mounting shelf (1355), in a location on top of the shelf, as an extension of the support (1357) and any combination thereof. Additionally or alternatively, the venting module comprises a plurality of air streaming means (e.g. fan). The air is streamed (1395) through an opening (air inlet) in the base of the cart (1310) by a fan (1372) located at the cart base. The air is further streamed through at least one air turbulating means (1390) located near at least one air streaming means. The air is further streamed through the cart support, additionally or alternatively, by a fan (1370, 1371).

The air can be streamed through at least one air entry port (1380). In this embodiment the noise reaching the neonate is attenuated due to the location of the venting module in the cart relatively far from the neonate placed within the PNTI. Additionally or alternatively, the air can be streamed in the other way around, entering the PNTI though at least some of the perforations (1330), and streamed through an air exit port (1380) to the cart through the support to the cart base and out to the external space. In this embodiment the cart is in fluid connection with the PNTI. Additionally or alternatively, the PNTI comprises at least one sound attenuating mean. Additionally or alternatively, the PNTI and cart are comprised of MRI safe materials. Additionally or alternatively, the cart and PNTI comprise life support equipment and or connections/ports for such equipment.

The cart in connection to the PNTI is configured by means of size and shape to be at least partly inserted into an MRD, a scanning device, an operating device, a treatment device, thereby enabling thermo regulating and/or venting of the neonate during examination. The PNTI is further permeable to the relevant means conducting the imaging/examination, such as RF, magnetic field, X ray, thermal reading means, infrared, radiation, and etc. Additionally or alternatively, the venting module is connected to a regulator configured to regulate the air streamed actively with the vent in accordance to a predetermined value, a value feed backed from at least one sensor, a manual command with a controller, and any combination thereof.

In this embodiment, the neonate/patient is located optimally in an imaging device, as close as possible to the original imaging device patient table, this is due to the PNTI being thermo regulated/vented with equipment placed remotely from the PNTI, therefore not adding volume to the top, bottom, back of the PNTI.

According to yet another embodiment of the invention, one or more upper thermo regulating modules located e.g., on support are provided for venting, heating, humidifying and filtering ambient air and flowing it via upper proximal aperture, upper zone in the canopy and via upper aperture by exit flow. Additionally or alternatively, a plurality of lower thermo regulating modules located e.g., on support are provided for venting, heating, humidifying and filtering ambient air and flowing it via lower proximal aperture, lower zone of the incubator and via lower aperture by exit flow.

According to one embodiment of the invention, a passive neonatal transport incubator (PNTI), useful for thermoregulating a neonate, comprising an inner volume configured by means of size and shape to accommodate the neonate, the inner volume is defined by an envelope having a main longitudinal axis with a proximal end and an opposite distal end; wherein the envelope is at least partially perforated; further wherein the PNTI is configured to be ventilated by an independently ventilated medical device.

According to one embodiment of the invention, a passive neonatal transport incubator (PNTI), useful for thermoregulating a neonate, comprising an inner volume configured by means of size and shape to accommodate the neonate, the inner volume is defined by an envelope having a main longitudinal axis with a proximal end and an opposite distal end; wherein the envelope is at least partially perforated; further wherein the PNTI is configured to be ventilated by an independently ventilated medical device; further wherein the medical device is selected from a group consisting of: incubator, cart, magnetic resonance device (MRD), CT scanner, X-ray device, ultrasonography device, elastography, fluoroscopy device, photoacoustic imaging device, thermography device, functional near-infrared spectroscopy, medical photography device and nuclear medicine functional imaging device, positron emission tomography (PET) device, operating table, treatment table, and any combination thereof.

According to one embodiment of the invention, a passive neonatal transport incubator (PNTI), useful for thermoregulating a neonate, comprising an inner volume configured by means of size and shape to accommodate the neonate, the inner volume is defined by an envelope having a main longitudinal axis with a proximal end and an opposite distal end; wherein the envelope is at least partially perforated; further wherein the PNTI is configured to be ventilated by an independently ventilated medical device; further wherein the medical device is selected from a group consisting of: incubator, cart, magnetic resonance device (MRD), CT scanner, X-ray device, ultrasonography device, elastography, fluoroscopy device, photoacoustic imaging device, thermography device, functional near-infrared spectroscopy, medical photography device and nuclear medicine functional imaging device, positron emission tomography (PET) device, operating table, treatment table, and any combination thereof; further wherein the PNTI is configured by means of size and shape to be inserted into an MRD bore, placed on a patient table of a medical device, placed instead of a patient table of a medical device, or any combination thereof.

According to one embodiment of the invention, a passive neonatal transport incubator (PNTI), useful for thermoregulating a neonate, comprising an inner volume configured by means of size and shape to accommodate the neonate, the inner volume is defined by an envelope having a main longitudinal axis with a proximal end and an opposite distal end; wherein the envelope is at least partially perforated; further wherein the PNTI is configured to be ventilated by an independently ventilated medical device; further wherein at least one of the following holds true: (a) the envelope is permeable in a manner selected from a group consisting of unidirectional, bidirectional and any combination thereof; (b) the perforations are at least partly permeable to ventilation; and, (c) the PNTI is permeable to radiation selected from a group consisting of alpha, beta, gamma, x-ray, magnetic, ionizing, thermal, infrared, sound, and any combination thereof; further wherein the PTI additionally comprising air turbulating means (ATM) for slowing and moderating airflow.

According to one embodiment of the invention, a passive neonatal transport incubator (PNTI), useful for thermoregulating a neonate, comprising an inner volume configured by means of size and shape to accommodate the neonate, the inner volume is defined by an envelope having a main longitudinal axis with a proximal end and an opposite distal end; wherein the envelope is at least partially perforated; further wherein the PNTI is configured to be ventilated by an independently ventilated medical device; further wherein the medical device is selected from a group consisting of: incubator, cart, magnetic resonance device (MRD), CT scanner, X-ray device, ultrasonography device, elastography, fluoroscopy device, photoacoustic imaging device, thermography device, functional near-infrared spectroscopy, medical photography device and nuclear medicine functional imaging device, positron emission tomography (PET) device, operating table, treatment table, and any combination thereof; further wherein the PNTI is configured by means of size and shape to be inserted into an MRD bore, placed on a patient table of a medical device, placed instead of a patient table of a medical device, or any combination thereof; further wherein at least a portion of the PNTI is made of MRI-safe materials; further wherein at least a portion of the PNTI comprises materials selected from a group consisting of: vibration absorptive, sound absorptive, liquid resistant, fire resistant, recyclable materials, disposable materials, at least partially transparent materials, flexible materials and any combination thereof.

According to one embodiment of the invention, a passive neonatal transport incubator (PNTI), useful for thermoregulating a neonate, comprising an inner volume configured by means of size and shape to accommodate the neonate, the inner volume is defined by an envelope having a main longitudinal axis with a proximal end and an opposite distal end; wherein the envelope is at least partially perforated; further wherein the PNTI is configured to be ventilated by an independently ventilated medical device; further wherein at least one of the following holds true: (a) the PNTI comprises at least one port configured for the docking or passage of life support equipment, tubing or both; (b) the PNTI comprises at least one opening for inserting the neonate; (c) the PNTI comprises at least one opening configured to allow entrance of a handler's hand; and, (d) the PNTI additionally comprising a reversibly attachable imperforated layer outside the envelope; further wherein the PTI as described above, additionally comprising at least one temperature regulating vent (TRV) in fluid communication with the PNTI.

According to one embodiment of the invention, a passive neonatal transport incubator (PNTI), useful for thermoregulating a neonate, comprising an inner volume configured by means of size and shape to accommodate the neonate, the inner volume is defined by an envelope having a main longitudinal axis with a proximal end and an opposite distal end; wherein the envelope is at least partially perforated; further wherein the PNTI is configured to be ventilated by an independently ventilated medical device; further wherein at least one of the following holds true: (a) the PNTI comprises at least one port configured for the docking or passage of life support equipment, tubing or both; (b) the PNTI comprises at least one opening for inserting the neonate; (c) the PNTI comprises at least one opening configured to allow entrance of a handler's hand; and, (d) the PNTI additionally comprising a reversibly attachable imperforated layer outside the envelope; further wherein the PTI as described above, additionally comprising at least one temperature regulating vent (TRV) in fluid communication with the PNTI; further wherein at least one of the following holds true: (a) the TRV is located at least one of the ends; further wherein the TRV is configured to stream air from the end towards the opposite end substantially along the axis; further wherein the PNTI is configured, by means of size and shape, to accommodate the neonate in parallel to the axis; (b) the TRV is a module selected from a group consisting of at least one first venting module, at least one first heating/cooling module, at least one air filter located adjacently to either the first venting module or the first heating/cooling module and any combination thereof; (c) the TRV comprises at least one venting module configured to introduce air selected from a group consisting of: heated air, cooled air, humidified air, filtered air, room temperature air, predetermined gas concentrated air, and any combination thereof into the PNTI; (d) the TRV comprises a feedback mechanism for the air quality selected from a group consisting of: temperature, humidity, pressure, airborne particle content, gas concentration, and any combination thereof, configured to maintain the quality in a predetermined value or value range; (e) the TRV is a fan, having at least one rotor rotating perpendicularly to a rotor's shaft, and further wherein the shaft is positioned in parallel to the PNTI's main longitudinal axis; (f) the TRV is configured to provide linear air flow, turbulent air flow or both within at least a portion of the PNTI inner volume; (g) the PNTI, the TRV or both comprising sound attenuating means, configured to at least partially attenuate the sound of the TRV, air movement within the PNTI, sound generated by an MRD, sound external to the PNTI, sound generated by the entrance of air into the PNTI, or any combination thereof; (h) the TRV is comprised of at least one venting module located at: the mobile base, at least one support, at least one PNTI end, or any combination thereof; further wherein the venting module is connected to the PNTI by at least one tubing; (i) the PNTI comprises a central processing unit (CPU); further wherein the CPU is configured to control a selected from a group consisting of: the TRV, control the TRV by responding to signals received from at least one sensor, control the TRV according to values defined by the user, control the TRV according to predefined physical condition of the neonate, and any combination thereof; and, (j) the TRV is: one first TRV located in one of the ends and at least one second TRV located in the opposite end, at least one TRV is located within the PNTI, at least one TRV is located outside the PNTI and is in fluid communication with the PNTI by means of a tubing; at least one TRV is in fluid communication with the PNTI, or at least one TRV is located remotely from the PNTI.

According to one embodiment of the invention, a passive neonatal transport incubator (PNTI), useful for thermoregulating a neonate, comprising an inner volume configured by means of size and shape to accommodate the neonate, the inner volume is defined by an envelope having a main longitudinal axis with a proximal end and an opposite distal end; wherein the envelope is at least partially perforated; further wherein the PNTI is configured to be ventilated by an independently ventilated medical device; further wherein at least one of the following holds true: (a) the PNTI comprises at least one port configured for the docking or passage of life support equipment, tubing or both; (b) the PNTI comprises at least one opening for inserting the neonate; (c) the PNTI comprises at least one opening configured to allow entrance of a handler's hand; and, (d) the PNTI additionally comprising a reversibly attachable imperforated layer outside the envelope; further wherein the PTI as described above, additionally comprising at least one temperature regulating vent (TRV) in fluid communication with the PNTI; further wherein the PNTI is in air communication with at least one air recycling mechanism (ARM); the ARM comprising: (a) at least one air inlet for collecting air stream from the PNTI's outer environment towards the PNTI's inner environment; and, (b) at least one recycled-air outlet for collecting air streamed from the PNTI's inner environment; further wherein at least one of the following is held true: (a) the PNTI additionally comprising at least one air flow regulator for regulating at least one air stream selected from a group consisting of: recycled air stream, air stream from the PNTI's outer environment, air streamed towards the PNTI's inner environment, and any combination thereof; (b) the PNTI additionally comprises: at least one air baffler, at least one air filter, or any combination thereof; (c) the PNTI is configured to direct the airflow drift to bypass the location of the neonate residing within; and, (d) the PNTI, is in fluid connection to externally supplied pressurized gas. It is another object of the current invention to disclose the PTI as described above, wherein the PNTI is interconnected to an MRI-safe cart.

According to one embodiment of the invention, a passive neonatal transport incubator (PNTI), useful for thermoregulating a neonate, comprising an inner volume configured by means of size and shape to accommodate the neonate, the inner volume is defined by an envelope having a main longitudinal axis with a proximal end and an opposite distal end; wherein the envelope is at least partially perforated; further wherein the PNTI is configured to be ventilated by an independently ventilated medical device; further wherein at least one of the following holds true: (a) the PNTI comprises at least one port configured for the docking or passage of life support equipment, tubing or both; (b) the PNTI comprises at least one opening for inserting the neonate; (c) the PNTI comprises at least one opening configured to allow entrance of a handler's hand; and, (d) the PNTI additionally comprising a reversibly attachable imperforated layer outside the envelope; further wherein the PTI as described above, additionally comprising at least one temperature regulating vent (TRV) in fluid communication with the PNTI; further wherein at least one of the following holds true: (a) the TRV is located at least one of the ends; further wherein the TRV is configured to stream air from the end towards the opposite end substantially along the axis; further wherein the PNTI is configured, by means of size and shape, to accommodate the neonate in parallel to the axis; (b) the TRV is a module selected from a group consisting of at least one first venting module, at least one first heating/cooling module, at least one air filter located adjacently to either the first venting module or the first heating/cooling module and any combination thereof; (c) the TRV comprises at least one venting module configured to introduce air selected from a group consisting of: heated air, cooled air, humidified air, filtered air, room temperature air, predetermined gas concentrated air, and any combination thereof into the PNTI; (d) the TRV comprises a feedback mechanism for the air quality selected from a group consisting of: temperature, humidity, pressure, airborne particle content, gas concentration, and any combination thereof, configured to maintain the quality in a predetermined value or value range; (e) the TRV is a fan, having at least one rotor rotating perpendicularly to a rotor's shaft, and further wherein the shaft is positioned in parallel to the PNTI's main longitudinal axis; (f) the TRV is configured to provide linear air flow, turbulent air flow or both within at least a portion of the PNTI inner volume; (g) the PNTI, the TRV or both comprising sound attenuating means, configured to at least partially attenuate the sound of: the TRV, air movement within the PNTI, sound generated by an MRD, sound external to the PNTI, sound generated by the entrance of air into the PNTI, or any combination thereof; (h) the TRV is comprised of at least one venting module located at: the mobile base, at least one support, at least one PNTI end, or any combination thereof; further wherein the venting module is connected to the PNTI by at least one tubing; (i) the PNTI comprises a central processing unit (CPU); further wherein the CPU is configured to control the TRV, control the TRV by responding to signals received from at least one sensor, control the TRV according to values defined by the user, control the TRV according to predefined physical condition of the neonate, or any combination thereof; and, (j) the TRV is: one first TRV located in one of the ends and at least one second TRV located in the opposite end, at least one TRV is located within the PNTI, at least one TRV is located outside the PNTI and is in fluid communication with the PNTI by means of a tubing; and, at least one TRV is in fluid communication with the PNTI, or at least one TRV is located remotely from the PNTI; further wherein the PNTI comprises at least one air entry port in connection with: an external venting module, an external humidifier, tubing, external air purifier, external heating/cooling device, external evaporated drug administrating device, or any combination thereof; further wherein at least one of the following is held true: (a) at least one of the perforations is configured to receive a signal and respond by at least partially opening or closing the perforation; (b) at least one of the perforations is adjustable in a manner selected from a group consisting of: size, amount, location, and any combination thereof; (c) at least one of the perforations is at least partially sealable; (d) at least one of the perforations is connected to a maneuverable baffle; (e) at least one of the perforations comprise at least one air filter; (f) at least one of the perforations is configured by means of size and shape to attenuate a predetermined sound; and, (g) at least one of the perforations is configured to direct the airflow drift to bypass the location of the neonate residing within.

According to one embodiment of the invention, a passive neonatal transport incubator (PNTI), useful for thermo-regulating a neonate, comprising an inner volume configured by means of size and shape to accommodate the neonate, the inner volume is defined by an envelope having a main longitudinal axis with a proximal end and an opposite distal end; wherein the envelope is at least partially perforated; further wherein the PNTI is configured to be ventilated by an independently ventilated medical device; further wherein at least one of the following holds true: (a) the PNTI comprises at least one port configured for the docking or passage of life support equipment, tubing or both; (b) the PNTI comprises at least one opening for inserting the neonate; (c) the PNTI comprises at least one opening configured to allow entrance of a handler's hand; and, (d) the PNTI additionally comprising a reversibly attachable imperforated layer outside the envelope; further wherein the PTI as described above, additionally comprising at least one temperature regulating vent (TRV) in fluid communication with the PNTI; further wherein the PNTI comprises sound attenuating means configured to at least partially attenuate: the sound of air flow into the PNTI, the sounds generated by the MRD the sound of air flow within the PNTI, the sounds generated by the external environment, or any combination thereof; further wherein the PNTI comprises at least one sensor selected from a group consisting of: a temperature sensor, a motion sensor, a breathing sensor, a gas concentration sensor, an air flow sensor, a humidity sensor, a door opening or closing sensor, a weight sensor, an RF sensor, an air pressure sensor, a cardiovascular activity sensor, a magnetic field sensor, a radiation sensor, and any combination thereof; further wherein at least one of the following holds true: (a) the PNTI comprises a central processing unit (CPU); (b) the PNTI additionally comprising a CPU configured to control the air flow passing through the perforation in response to a predetermined value of a parameter of the PNTI inner volume selected from a group consisting of: information from at least one sensor, air pressure, temperature, humidity, sound levels, gas concentration, airborne particle count, and any combination thereof.

According to one embodiment of the invention, a passive neonatal transport incubator (PNTI), useful for thermo-regulating a neonate, comprising an inner volume configured by means of size and shape to accommodate the neonate, the inner volume is defined by an envelope having a main longitudinal axis with a proximal end and an opposite distal end; wherein the envelope is at least partially perforated; further wherein the PNTI is configured to be ventilated by an independently ventilated medical device; further wherein at least one of the following holds true: (a) the PNTI comprises at least one port configured for the docking or passage of life support equipment, tubing or both; (b) the PNTI comprises at least one opening for inserting the neonate; (c) the PNTI comprises at least one opening configured to allow entrance of a handler's hand; and, (d) the PNTI additionally comprising a reversibly attachable imperforated layer outside the envelope; further wherein the PTI as described above, additionally comprising at least one temperature regulating vent (TRV) in fluid communication with the PNTI; further wherein at least a portion of the PNTI's walls are double jacket walls arrangement (DJW), comprising an inner wall and an outer wall; the DJW comprising at least partly perforated inner-wall and an intact non-perforated outer-wall, or the outer wall and the inner wall are both at least partly perforated, thereby the DJW facilitating the air stream, along the main longitudinal axis in a conduit having a predefined width (w) and length (l); further wherein the conduit between the double jacket walls comprises: sound attenuating means, thermal isolating materials, vibration reducing means, RF coils, conductive material, non-conductive material, or any combination thereof; further wherein at least a portion of the width and the length (w, l) are equal along the longitudinal axis, changes along the longitudinal axis, or any combination thereof.

The invention claimed is:

1. A passive neonatal transport incubator (PNTI), useful for thermo-regulating a neonate, comprising:
    an inner volume configured by means of size and shape to accommodate said neonate, said inner volume is defined by an envelope having a main longitudinal axis with a proximal end and an opposite distal end, wherein said envelope is perforated by at least one perforation and wherein said PNTI is configured to be inserted into an imaging device, said imaging device comprising a venting module and said PNTI is configured to be ventilated by said venting module through said perforated envelope, and wherein said PNTI comprises one or more sensors including a temperature sensor; and
    a mechanism configured to open and close the at least one perforation, the at least one perforation is configured to be opened or closed based on a signal received by said mechanism from said at least one sensor or more sensors, and wherein said mechanism is a hatch, shutter, flexible material, or shape changing polymer.

2. The PNTI according to claim 1, wherein said imaging medical device is selected from the group consisting of a magnetic resonance device (MRD), a CT scanner, an X-ray device, an ultrasonography device, an elastography, fluoroscopy device, a photoacoustic imaging device, a thermography device, a functional near-infrared spectroscopy, a medical photography device and a nuclear medicine functional imaging device, a positron emission tomography (PET) device, and any combination thereof.

3. The PNTI according to claim 1, wherein said imaging device is a magnetic resonance device (MRD) having a bore and wherein said PNTI is made of MRI-safe materials and is configured by means of size and shape to be inserted into said bore.

4. The PNTI according to claim 1, wherein said PNTI is permeable to radiation selected from the group consisting of alpha, beta, gamma, x-ray, magnetic, ionizing, thermal, infrared, sound, and any combination thereof.

5. The PNTI according to claim 1, wherein the one or more sensors are a a temperature sensor, a motion sensor, a breathing sensor, a gas concentration sensor, an air flow sensor, a humidity sensor, a door opening or closing sensor, a weight sensor, an RF sensor, an air pressure sensor, a cardiovascular activity sensor, a magnetic field sensor, a radiation sensor, or any combination thereof.

6. The PNTI according to claim 1, additionally comprising air turbulating means (ATM) configured for slowing and moderating airflow.

7. The PNTI according to claim 1, wherein at least a portion of said PNTI comprises materials selected from a group consisting of: vibration absorptive, sound absorptive, liquid resistant, fire resistant, recyclable materials, disposable materials, at least partially transparent materials, flexible materials and any combination thereof.

8. The PNTI according to claim 1, wherein at least one of the following holds true:
 a. said PNTI comprises at least one port configured for the docking or passage of life support equipment, tubing or both;
 b. said PNTI comprises at least one opening for inserting said neonate;
 c. said PNTI comprises at least one opening configured to allow entrance of a handler's hand; and,
 d. said PNTI comprises a reversibly attachable imperforated layer outside said envelope.

9. The PNTI according to claim 1, wherein said PNTI is in air communication with at least one air recycling mechanism (ARM); said ARM comprising:
 a. at least one air inlet for collecting air stream from said PNTI's outer environment towards said PNTI's inner environment; and,
 b. at least one recycled-air outlet for collecting air streamed from said PNTI's inner environment.

10. The PNTI according to claim 1, wherein at least one of the following is held true:
 a. said PNTI additionally comprises at least one air baffler, at least one air filter, or any combination thereof;
 b. said PNTI, is in fluid connection to externally supplied pressurized gas.

11. The PNTI according to claim 1, wherein said PNTI is interconnected to an MRI-safe cart.

12. The PNTI according to claim 1, wherein said PNTI comprises at least one air entry port in connection with an external device elected from a group consisting of: a venting module, a humidifier, tubing, an air purifier, a heating/cooling device, and any combination thereof.

13. The PNTI according to claim 1, wherein at least one of the following is held true:
 a. at least one of said perforations is configured to receive a signal and respond by at least partially opening or closing said perforation;
 b. at least one of said perforations is adjustable in a manner selected from a group consisting of: size, amount, location, and any combination thereof;
 c. at least one of said perforations is at least partially sealable;
 d. at least one of said perforations is connected to a maneuverable baffle;
 e. at least one of said perforations comprise at least one air filter;
 f. at least one of said perforations is configured by means of size and shape to attenuate a predetermined sound; and
 g. at least one of said perforations is configured to direct an airflow drift to bypass the location of said neonate residing within.

14. The PNTI according to claim 1, wherein at least a portion of walls of the PNTI are double jacket walls arrangement (DJW), comprising an inner wall and an outer wall forming a conduit therebetween; said conduit having a predefined width (w) and length (l) said outer wall and said inner wall are both at least partly perforated, thereby said DJW facilitating air stream, along the main longitudinal axis in a conduit.

15. The PNTI according to claim 14, wherein said conduit comprises sound attenuating means, thermal isolating materials, vibration reducing means, RF coils, conductive material, non-conductive material, or any combination thereof.

16. A method for passively thermo-regulating a neonate, characterized by
 a. obtaining a passive neonatal transport incubator (PNTI) according to claim 1;
 b. accommodating said neonate in said PNTI; and
 c. introducing said PNTI in a thermo-regulated environment.

17. The method of claim 16, additionally comprising the step of inserting said PNTI into a ventilated medical device; said medical device is selected from a group consisting of: incubator, cart, magnetic resonance device (MRD), CT scanner, X-ray device, ultrasonography device, elastography, fluoroscopy device, photoacoustic imaging device, thermography device, functional near-infrared spectroscopy, medical photography device and nuclear medicine functional imaging device, positron emission tomography (PET) device, operating table, treatment table, and any combination thereof.

* * * * *